(12) United States Patent
Nagano et al.

(10) Patent No.: US 7,868,147 B2
(45) Date of Patent: Jan. 11, 2011

(54) FLUORESCENT PROBE

(75) Inventors: Tetsuo Nagano, 1-28-15, Amanuma, Suginami-ku, Tokyo, 167-0032 (JP); Mako Kamiya, Ibaraki (JP); Yasuteru Urano, Kanagawa (JP)

(73) Assignees: Tetsuo Nagano, Tokyo (JP); Sekisui Medical Co., Ltd., Tokyo (JP)

( * ) Notice: Subject to any disclaimer, the term of this patent is extended or adjusted under 35 U.S.C. 154(b) by 812 days.

(21) Appl. No.: 10/570,355

(22) PCT Filed: Sep. 3, 2004

(86) PCT No.: PCT/JP2004/013185
§ 371 (c)(1), (2), (4) Date: Mar. 26, 2007

(87) PCT Pub. No.: WO2005/024049
PCT Pub. Date: Mar. 17, 2005

(65) Prior Publication Data
US 2008/0014602 A1 Jan. 17, 2008

(30) Foreign Application Priority Data
Sep. 5, 2003 (JP) .............................. 2003-314041

(51) Int. Cl.
*C07H 15/24* (2006.01)
*C07D 311/82* (2006.01)
*C07D 501/30* (2006.01)
*C07F 9/12* (2006.01)

(52) U.S. Cl. ....................... 536/18.1; 540/222; 549/220; 549/388; 435/18; 435/19; 435/21

(58) Field of Classification Search ................. 536/18.1; 540/222; 549/220, 388
See application file for complete search history.

(56) References Cited

U.S. PATENT DOCUMENTS

| | | | |
|---|---|---|---|
| 5,874,590 A | 2/1999 | Nagano et al. | |
| 6,903,226 B2 | 6/2005 | Nagano et al. | |
| 7,087,766 B2 | 8/2006 | Nagano et al. | |
| 7,524,974 B2 | 4/2009 | Nagano et al. | |
| 7,696,245 B2 | 4/2010 | Komatsu et al. | |
| 2003/0153027 A1 | 8/2003 | Nagano et al. | |
| 2003/0162298 A1 | 8/2003 | Nagano et al. | |
| 2004/0054195 A1* | 3/2004 | Gao et al. ................... | 549/223 |
| 2005/0037332 A1 | 2/2005 | Komatsu et al. | |
| 2006/0030054 A1 | 2/2006 | Nagano et al. | |
| 2008/0249321 A1 | 10/2008 | Nagano et al. | |

FOREIGN PATENT DOCUMENTS

| | | |
|---|---|---|
| DE | 295 855 | 11/1991 |
| EP | 1260508 | 11/2002 |
| JP | 10-226688 | 8/1998 |
| WO | 01/62755 | 8/2001 |
| WO | 01/64664 | 9/2001 |
| WO | 2004/005917 | 1/2004 |
| WO | 2005/085811 | 9/2005 |

OTHER PUBLICATIONS

Gao et al, Analytical Chem. vol. 74, No. 24, p. 6397-6401 (2002).*
D. Tadic et al., "Chiral Prodyes. Ethers and Esters of Dihydrofluorescein, Part 1: Dibenzyldihydrofluorescein (DBDF) A New Reagent", Heterocycles, 1990, vol. 31, No. 11, pp. 1975-1982.
An English language abstract JP 10-226688, (1987).
An English language abstract WO 2004/005917, (2004).
L. Lindqvist et al., "Radiationless Transitions in Xanthene Dyes", J. Chem. Phys., vol. 44, pp. 1711-1712 (1966).
U.S. Appl. No. 10/598,371 to Nagano et al., (2008).
"Gendaikagaku", Dec. 2002 (No. 381), p. 44-50.
Office Action in counterpart Japanese Patent Application 2005-513726 dated Jul. 13, 2010.
Supplementary European Search Report for European Application No. 04772924.9, (2009).
Miura, Journal of American Chemical Society, (2003), vol. 125, No. 28, pp. 8666-8671.
Fogl, J. et al., Scientific Papers of the Prague Institute of Chemical Technology. Chemical Engineering, (1981), vol. H-16, pp. 17-39.
Fedin, A. et al., Kristoallografia, (1975), vol. 20, No. 1, pp. 163-166.

* cited by examiner

*Primary Examiner*—Bernard Dentz
(74) *Attorney, Agent, or Firm*—Greenblum & Bernstein, P.L.C.

(57) ABSTRACT

A fluorescent probe which is represented by the following formula (I):

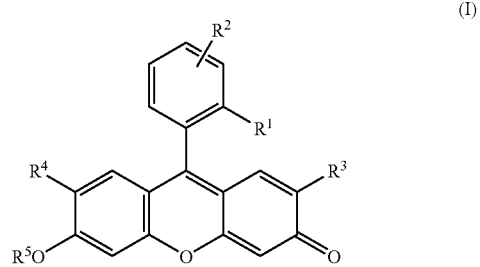

(wherein, $R^1$ represents a monovalent substituent other than hydrogen atom, carboxy group, or sulfo group; $R^2$ represents hydrogen atom, or a monovalent substituent; $R^3$ and $R^4$ each independently represents hydrogen atom or a halogen atom; and $R^5$ represents a monovalent group which is cleaved by contact with a measuring object, provided that a combination of $R^1$ and $R^2$ is selected so that the oxidation potential of the benzene ring to which they bind makes (1) the compound represented by the formula (I) substantially no fluorescent before the cleavage, and (2) a compound after the cleavage, which is derived from the compound represented by the formula (I), substantially highly fluorescent after the cleavage).

10 Claims, 11 Drawing Sheets

Conceptual diagram of PET

} PET donor
- controlling fluorescence intensity
- trapping object to be analyzed } Fluorophore
- determining absorption and fluorescence wavelength

Fluorescein

HEK293 / +lacZ

HEK293 / -lacZ

FLUORESCENT PROBE

TECHNICAL FIELD

The present invention relates to a fluorescent probe. More specifically, the present invention relates to a fluorescent probe which traps a target substance such as an enzyme and emits fluorescence.

BACKGROUND ART

Fluorescein, a fluorescent substance known from the 19th century, can be excited at around 500 nm in an aqueous solution, and has a high quantum yield. For this reason, the substance has been commonly used as a fundamental scaffold of fluorescent probes. For example, fluorescein is used as a fundamental nucleus of a fluorescent probe for nitrogen monoxide (Japanese Patent Laid-Open No. 10-226688 (1998)), a fluorescent probe for zinc (WO 01/62755), or the like.

6-Hydroxy-9-phenylfluorone, in which the carboxy group of fluorescein is substituted with hydrogen atom, has a lower fluorescence quantum yield. Accordingly, the carboxy group is believed to have a role in characteristics as a fluorophore of fluorescein (Lindqvist, L., et al., J. Chem. Phys., 44, 1711-12, 1966). From the above reason, the carboxy group is preserved in fluorescein derivatives proposed so far to avoid deterioration of the fluorescent property of fluorescein. Therefore, almost no compound is known wherein the carboxy group is converted to other functional group.

DISCLOSURE OF THE INVENTION

An object of the present invention is to provide a fluorescent probe with an excellent fluorescence property. The inventors of the present invention conducted various researches on characteristics of fluorescein as an fluorescent substance, and during the course of the researches, they have come to a conclusion that the fluorescence properties of fluorescein essentially derive from the tricyclic xanthene skeleton, and the 2-carboxyphenyl group binding to the 9-position of the xanthene ring has absolutely no substantial effect on the fluorescence properties. The inventors of the present invention evaluated fluorescence properties of compounds wherein the carboxy group of the 2-carboxyphenyl group is substituted with a substituent other than hydrogen atom, such as methyl group or methoxy group. Surprisingly, they found that the compounds had intensities of fluorescence quantum yield almost equal to that of fluorescein, and the compounds had almost the same excitation wavelength and fluorescence wavelength as those of fluorescein.

On the basis of the above findings and the fact that 6-hydroxy-9-phenylfluorone, in which the carboxy group of fluorescein is replaced with hydrogen atom, gave a lowered fluorescence quantum yield, the inventors of the present invention concluded that a role of the carboxy group of fluorescein is to prevent a free rotation due to the carbon-carbon single bond between the xanthene ring and the benzene ring, thereby a pathway of deactivation of a fluorophore in an excitation state without a luminescence process can be prevented. Further, the inventors of the present invention conducted researches to develop a fluorescent probe having a high fluorescence property based on the above findings. As a result, they found that a compound, wherein the phenyl group which binds to the 9-position of the xanthene ring has sufficiently high electron density, is substantially non-fluorescent, whilst a compound wherein said phenyl group has sufficiently low electron density is highly fluorescent, and that a fluorescent probe having a desired fluorescence property can be logically designed by adjusting the electron density of said phenyl group with conversion of the carboxy group of fluorescein to other functional group, and filed a patent application for this invention (PCT/JP03/8585).

The inventors of the present invention further conducted various researches to provide different means for achieving the aforementioned object. As a result, they found that, when compounds whose hydroxy group of a xanthene ring was protonated or deprotonated were compared, each reduction potential of the xanthene ring gave a significant difference, and that by suitably choosing an electron density of the benzene ring moiety (electron donor moiety) to utilize the difference in the reduction potential as an ON/OFF switch of fluorescence, novel fluorescent probes were successfully provided in which a moiety for a reaction with a measuring object was introduced into the xanthene ring moiety. The present invention was achieved on the basis of the above findings.

The present invention thus provides a fluorescent probe which is represented by the following formula (I):

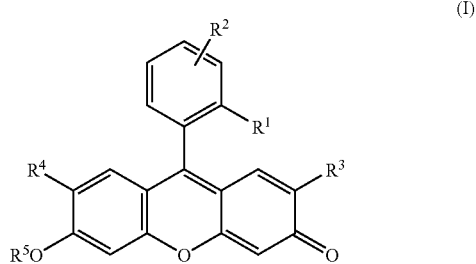

(wherein, $R^1$ represents a monovalent substituent other than hydrogen atom, carboxy group, or sulfo group; $R^2$ represents hydrogen atom, or a monovalent substituent; $R^3$ and $R^4$ each independently represents hydrogen atom or a halogen atom; and $R^5$ represents a monovalent group which is cleaved by contact with a measuring object, provided that a combination of $R^1$ and $R^2$ is selected so that the oxidation potential of the benzene ring to which they bind makes:

(1) the compound represented by the formula (I) substantially no fluorescent before the cleavage, and (2) a compound after the cleavage, which is derived from the compound represented by the formula (I), substantially highly fluorescent after the cleavage).

According to preferred embodiments of the present invention, provided are the aforementioned fluorescent probe, wherein the combination of $R^1$ and $R^2$ is selected so that the oxidation potential of said benzene ring is 1.55 to 1.75 V; and the aforementioned fluorescent probe, wherein the combination of $R^1$ and $R^2$ is selected so that the oxidation potential of said benzene ring is 1.60 to 1.70 V. According to further preferred embodiments of the present invention, provided are the aforementioned fluorescent probe, wherein $R^3$ and $R^4$ are hydrogen atoms; the aforementioned fluorescent probe, wherein $R^1$ is a lower alkyl group, and $R^2$ is a lower alkoxy group; the aforementioned fluorescent probe, wherein $R^1$ is a lower alkyl group, and $R^2$ is a lower alkoxy group at the para-position relative to the xanthene ring residue; the aforementioned fluorescent probe, wherein the cleavage is caused by hydrolysis; the aforementioned fluorescent probe, wherein the measuring object is a hydrolase; the aforementioned fluorescent probe, wherein $R^5$ is phosphono group that is cleaved by a phosphatase; the aforementioned fluorescent probe, wherein R⁵ is a residue of a saccharide derivative cleavable with a saccharide hydrolase; the aforementioned fluorescent probe, wherein R⁵ is β-galactopyranosyl group; the aforementioned fluorescent probe, wherein R⁵ is β-galactopyranosyl group, and R² is a carboxy-substituted alkoxy group, or 4-carboxybutoxy group; the aforementioned fluorescent probe, wherein R⁵ is a group containing a cyclic amide cleavable with a β-lactamase; and the aforementioned fluorescent probe, wherein the group containing a cyclic amide cleavable with a β-lactamase is a group represented by the following formula;

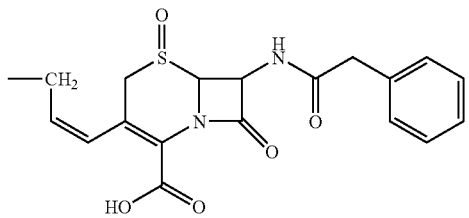

From another aspect, also provided by the present invention is a method for designing a fluorescent probe represented by the aforementioned formula (I) (wherein, R¹, R², R³, R⁴, and R⁵ have the same meanings as those defined above, respectively), which comprises the step of selecting a combination of R¹ and R² so that the oxidation potential of the benzene ring to which they bind makes:

(1) the compound represented by the formula (I) substantially no fluorescent before the cleavage, and
(2) a compound after the cleavage, which is derived from the compound represented by the formula (I), substantially highly fluorescent after the cleavage.

BEST MODE FOR CARRYING OUT THE INVENTION

Figure 1:
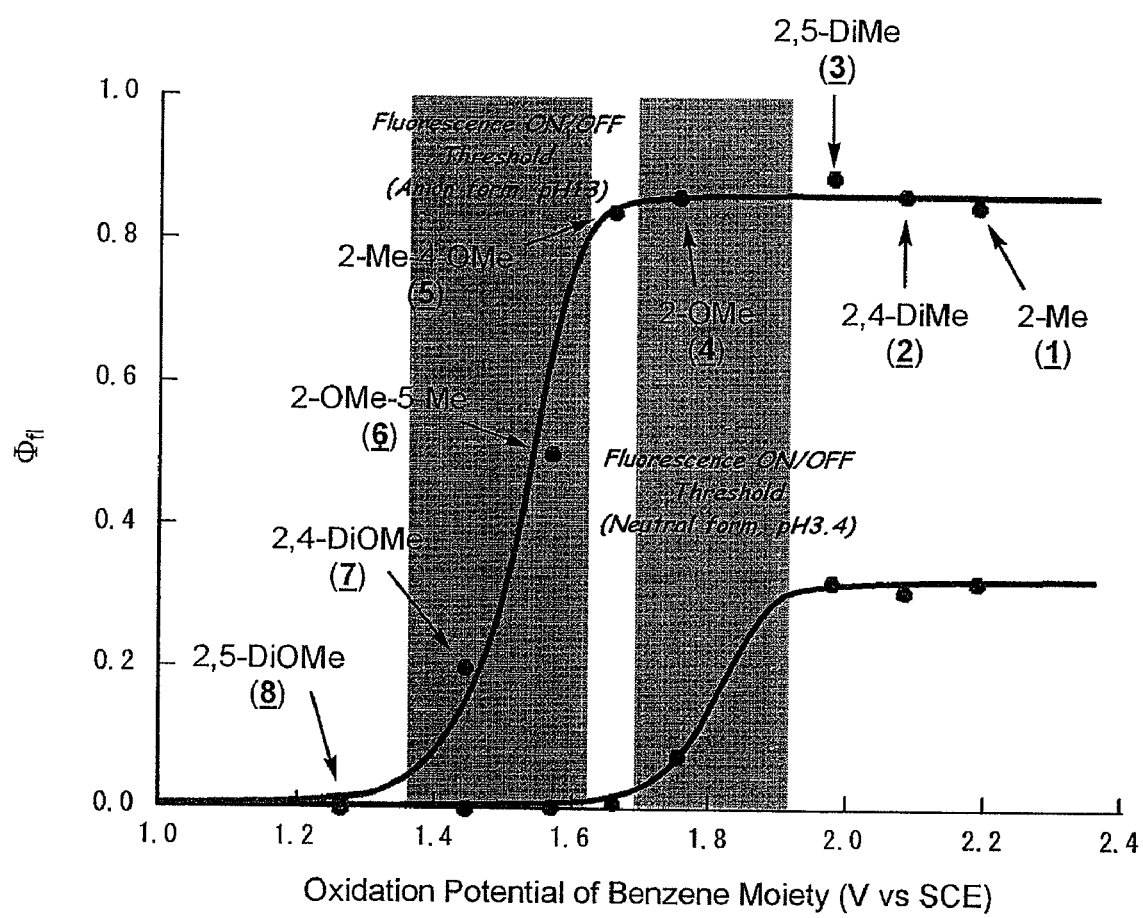
FIG. 1 shows, as for derivatives wherein the carboxy group of fluorescein is converted to an alkyl group or an alkoxy group (Compounds 1 to 8), a correlation between fluorescence quantum yield of each compound and oxidation potential of the benzene ring moiety as a PET donor.

The fluorescent probe provided by the present invention which is represented by the formula (I) can be cleaved by contact with a measuring object to produce a fluorescent compound (corresponding to a compound of the aforementioned formula (I) wherein R⁵ is cleaved, and the hydroxy group is present as an anion form), and therefore, used as a fluorescent probe for measurement of a measuring object. Type of the measuring object is not particularly limited, and the object may be any of metal ions (for example, alkali metal ions such as sodium ion and lithium ion, alkaline earth metal ions such as calcium ion, magnesium ion, and zinc ion), non-metal ions (carbonate ion and the like), active oxygen species (for example, nitrogen monoxide, hydroxyl radical, singlet oxygen, superoxide and the like) and the like. The measuring object is preferably an enzyme. Examples of the enzyme include, for example, reductases, oxidases, hydrolases, and the like. Specific examples include, for example, β-lactamase, cytochrome P450 oxidase, β-galactosidase, β-glucosidase, β-glucuronidase, β-hexosaminidase, lactase, alkaline phosphatase, and the like, but not limited to these examples. Among the enzymes, hydrolases are especially preferred. Typical examples of the hydrolases include, for example, β-galactosidase, β-lactamase, alkaline phosphatases, and the like. However, the hydrolases are not limited to the foregoing hydrolases.

The fluorescent probe of the present invention is characterized in that the carboxy group of the 2-carboxyphenyl group binding at the 9-position of the xanthene ring of various fluorescent probes for measuring variety of measuring objects, which have been proposed so far on the basis of the fundamental skeleton of fluorescein, is converted to a monovalent substituent other than hydrogen atom or sulfo group, and that the hydroxy group of the xanthene skeleton is used as the reaction site with a measuring object. The fluorescent probe of the present invention is characterized in that the probe, per se, is substantially no fluorescent, but the probe is cleaved by contact with a measuring object to produce a compound having a highly fluorescent property.

R¹ represents a monovalent substituent other than hydrogen atom, carboxy group, or sulfo group. R² represents hydrogen atom, or a monovalent substituent. Type of the monovalent substituent as these groups is not particularly limited. For example, an alkyl group is preferred as R¹, and an alkoxy group is preferred as R². The alkyl group as R¹, and the alkoxy group as R² may have one or more arbitrary substituents. Examples of the substituents of the alkoxy group as R² include, for example, a carboxy-substituted $C_{1-6}$ alkoxy group, an alkoxycarbonyl-substituted $C_{1-6}$ alkoxy group, and the like. In the specification, "an alkyl group" or an alkyl moiety of a substituent containing the alkyl moiety (for example, an alkoxy group) means, for example, a linear, branched, or cyclic alkyl group, or an alkyl group comprising a combination thereof having 1 to 12 carbon atoms, preferably 1 to 6 carbon atoms, more preferably 1 to 4 carbon atoms. More specifically, a lower alkyl group (an alkyl group having 1 to 6 carbon atoms) is preferred as the alkyl group. Examples of the lower alkyl group include methyl group, ethyl group, n-propyl group, isopropyl group, cyclopropyl group, n-butyl group, sec-butyl group, isobutyl group, tert-butyl group, cyclopropylmethyl group, n-pentyl group, and n-hexyl group. As $R^1$, a lower alkyl group is more preferred, and as $R^2$, a lower alkoxy group is more preferred. Particularly preferred is a compound wherein $R^1$ is methyl group, and $R^2$ is methoxy group. Further, a compound wherein $R^2$ is a monocarboxy-substituted $C_{1-6}$ alkoxy group, or a monoalkoxycarbonyl-substituted $C_{1-6}$ alkoxy group is also preferred. Particularly preferred is a compound wherein $R^1$ is 4-carboxybutoxy group, or 4-acetoxymethyloxycarbonylbutoxy group. The fluorescent probe of the present invention wherein $R^2$ is 4-acetoxymethyloxycarbonylbutoxy group has superior properties in that the probe is efficiently taken up into cells due to the high liposolubility thereof, and when taken up into cells, the 4-acetoxymethyloxy-carbonylbutoxy group is hydrolyzed by an esterase existing in the cells, and thereby the compound is converted into a highly water-soluble fluorescent probe and thus becomes likely to be retained in the cells. Therefore, the probe is especially suitable as a fluorescent probe for use in imaging of the inside of cells. Substituting position of $R^2$ on the benzene ring is not particularly limited. The position is preferably the para-position relative to the binding position of the residue of xantene ring. On the benzene ring to which $R^1$ and $R^2$ bind, arbitrary substituents other than these substituents may exist.

When the term "a halogen atom" is referred to in the specification, a halogen may be any one of fluorine atom, chlorine atom, bromine atom, or iodine atom, and preferably, fluorine atom, chlorine atom, or bromine atom. As the halogen atom represented by $R^3$ and $R^4$, chlorine atom or fluorine atom is preferred. $R^3$ and $R^4$ each independently is preferably hydrogen atom, chlorine atom, or fluorine atom. $R^5$ can be appropriately chosen depending on a combination with a measuring object so as to be readily cleaved. For example, when the measuring object is a saccharide hydrolase, a residue of the saccharide compound serving as a substrate of the enzyme can be used as $R^5$. Functional groups of the saccharide compound such as hydroxy group and amino group may be protected with a protective group as required. Compounds having such a protective group all fall within the scope of the present invention.

In the fluorescent probe of the present invention, a combination of $R^1$ and $R^2$ is chosen so that (1) the compound represented by the formula (I) is substantially no fluorescent before the cleavage of $R^5$ by the measuring object, and (2) a compound derived from the compound represented by the formula (I) after the cleavage becomes substantially highly fluorescent after the cleavage of $R^5$ by the measuring object.

For the selection of a combination of $R^1$ and $R^2$, information of the electron density of the benzene ring to which they bind may be utilized. Information of the electron density of the benzene ring is easily available, for example, by calculating oxidation potential of said benzene ring according to a quantum chemical means. A reduction of the oxidation potential of said benzene ring means an increase of the electron density of said benzene ring, which corresponds to an elevation of HOMO orbital energy. For example, HOMO energy of said benzene ring moiety can be determined by a density functional theory (B3LYP/6-31G(d)). All the oxidation potentials described in the specification are indicated as values obtained with a saturated calomel electrode as a reference electrode, of which base line is different by about 0.24 V from that used for values obtained with a silver/silver nitrate electrode (Ag/Ag$^+$) as a reference electrode.

As specifically shown in Example 2 in the section of examples of the present specification, the hydroxy group on the xanthene ring of the compounds represented by the formula (I) wherein $R^5$ is hydrogen atom becomes an anion after dissociation of its proton in an aqueous alkaline solution at pH 13 or an aqueous neutral solution (i.e., the hydroxy group is present as —O$^-$). For example, under such a condition, a compound wherein oxidation potential of said benzene ring is 1.20 V or lower is substantially no fluorescent, whilst when the oxidation potential of said benzene ring is 1.60 V or higher, the compound may sometimes be substantially strongly fluorescent. Further, under an acidic condition at pH 3.4, the compound is in a state that a proton exists on the hydroxy group (i.e., the hydroxy group is present as —OH). For example, under such a condition, a compound wherein the oxidation potential of said benzene ring is 1.60 V or lower is substantially no fluorescent, whilst when the oxidation potential of said benzene ring is 1.90 V or higher, the compound may sometimes be substantially strongly fluorescent. This correlation is shown in FIG. 1. FIG. 1 shows changes in oxidation potential of the benzene ring for compounds having various combinations of $R^1$ and $R^2$, and fluorescence quantum yields of those compounds. The curves for pH 13 show the correlations between the oxidation potential and fluorescence quantum yield for deprotonated compounds, and the curves for pH 3.4 show the correlations between the oxidation potential and fluorescence quantum yield for protonated compounds.

It has been experimentally confirmed that the oxidation potentials of the benzene ring moiety of a compound wherein a proton is present on the hydroxy group and a compound wherein $R^5$ is, for example, an alkyl group or the like are substantially identical. Therefore, as the oxidation potential of the benzene ring moiety of a compound before the cleavage of $R^5$, oxidation potential of the benzene ring moiety of a compound represented by the formula (I) wherein $R^5$ is hydrogen atom placed under an acidic condition of pH 3.4 may be used. Accordingly, for choosing a preferred combination of $R^1$ and $R^2$ by using the oxidation potential of the benzene ring as a criterion, a combination can be selected so that, for a compound represented by the formula (I) wherein $R^5$ is hydrogen atom, difference in fluorescence quantum yields at pH 3.4 and 13 can become maximum, for example, by referring to FIG. 1. More specifically, it is preferable to select a combination of $R^1$ and $R^2$ so that the oxidation potential of the benzene ring becomes 1.55 to 1.75 V, more preferably 1.60 to 1.70 V, in FIG. 1. It is most preferable to select a combination of $R^1$ and $R^2$ so that the oxidation potential of the benzene ring is about 1.65 V. When one or more substituents other than $R^1$ and $R^2$ exist on the benzene ring to which $R^1$ and $R^2$ bind, the combination is preferably selected so that the oxidation potential of the benzene ring including all of $R^1$, $R^2$, and the substituent or substituents can be within the aforementioned range.

Although it is not intended to be bound by any specific theory, the above mentioned findings discovered by the inventors of the present invention can be explained by PET (Photoinduced Electron Transfer). PET is one of methods for fluorescence quenching, wherein electron transfer from neighboring electron donating moiety (PET donor) occurs to induce fluorescence quenching faster than a rate where the singlet-excited fluorophore generated by irradiation of excitation light returns to a ground state with fluorescence emission. When the compound represented by the formula (I) is divided for consideration as a xanthene ring moiety which acts as a fluorophore and a benzene ring moiety which quench the fluorescence (PET donor), if the oxidation potential of the benzene ring is low (i.e., higher electron density and higher HOMO energy), the fluorescence derived from the xanthene ring will be quenched through the PET.

As fluorescent probes, compounds are required to have a feature that the probe is substantially no fluorescent before cleavage of $R^5$ by a measuring object and changes to substantially strongly fluorescent substance after cleavage of $R^5$ by a measuring object. Therefore, a probe having a significant change in fluorescence intensity can be chosen as a preferable probe. For example, a probe can be designed so that its fluorescence is quenched through PET before the cleavage of $R^5$ by a measuring object and substantially no PET is induced after the cleavage of $R^5$ by a measuring object. In the method for designing a fluorescent probe of the present invention, a fluorescent probe can be designed by fixing the oxidation potential of the benzene ring, and utilizing the change in the oxidation potential observed for the xantene ring before and after the cleavage of $R^5$, so that the fluorescence can be quenched by PET before the cleavage of $R^5$, and the compound after the cleavage can emit strong fluorescence due to disturbance of PET after the cleavage.

The term "measurement" used in the present specification should be construed in its broadest sense, including quantification, qualification, measurements performed for the purpose of diagnosis, tests, detections and the like. The method for measuring a measuring object using the fluorescent probe of the present invention generally comprises (a) the step of bringing a compound represented by the aforementioned formula (I) into contact with a measuring object to cleave $R^5$; and (b) the step of measuring fluorescence of a compound generated in the aforementioned process (a) (corresponding to a compound of which $R^5$ is cleaved). For example, the fluorescent probe of the present invention or a salt thereof may be dissolved in an aqueous medium such as physiological saline or a buffered solution, or in a mixture of the aqueous medium and a water-miscible solvent such as ethanol, acetone, ethylene glycol, dimethyl sulfoxide, and dimethylformamide, the resultant solution may be added to a suitable buffered solution containing cells or tissues, and then the fluorescence spectra may be measured.

Fluorescence of the compounds after the cleavage of $R^5$ by a measuring object can be measured by an ordinary method. For example, a method of measuring fluorescence spectra in vitro, or a method of measuring fluorescence spectra in vivo by a bioimaging technique can be employed. For example, when a quantitative measurement is conducted, a calibration curve is desired to be prepared in advance according to an ordinary method.

As the fluorescent probe of the present invention, as well as the compound represented by the aforementioned formula (I), a salt thereof may be used. Types of the salt are not particularly limited. Examples of the salt include, for example, mineral acid salts such as hydrochloride, sulfate, and nitrate; and organic acid salts such as methanesulfonate, p-toluenesulfonate, oxalate, citrate, and tartrate as acid addition salts, and metal salts such as sodium salts, potassium salts, calcium salts, and magnesium salts; ammonium salts; and organic amine salts such as triethylamine salts as base addition salts. In addition, salts of amino acids such as glycine may be formed. The fluorescent probe according to the present invention may be used as a composition by mixing with additives generally used for regent preparation, if necessary. For example, as additives for use of the reagent under a physiological condition, additives such as dissolving aids, pH adjusters, buffers, isotonic agents and the like can be used, and amounts of these additives can suitably be chosen by those skilled in the art. The compositions may be provided as those in appropriate forms, for example, powdery mixtures, lyophilized products, granules, tablets, solutions and the like.

EXAMPLES

The present invention will be explained more specifically by referring to the following examples. However, the scope of the present invention is not limited to these examples.

Example 1

Synthesis of Compounds

The following compounds are synthesized. These compounds are designed so that a compound having greater compound number has a lower oxidation potential of the benzene ring binding at the 9-position of the xanthene ring (i.e., so as to have higher electron density, in other words, to have higher HOMO orbital energy). Synthetic schemes of the compound having unsubstituted benzene ring and Compound 1 are shown below (in the schemes, Me represents methyl group).

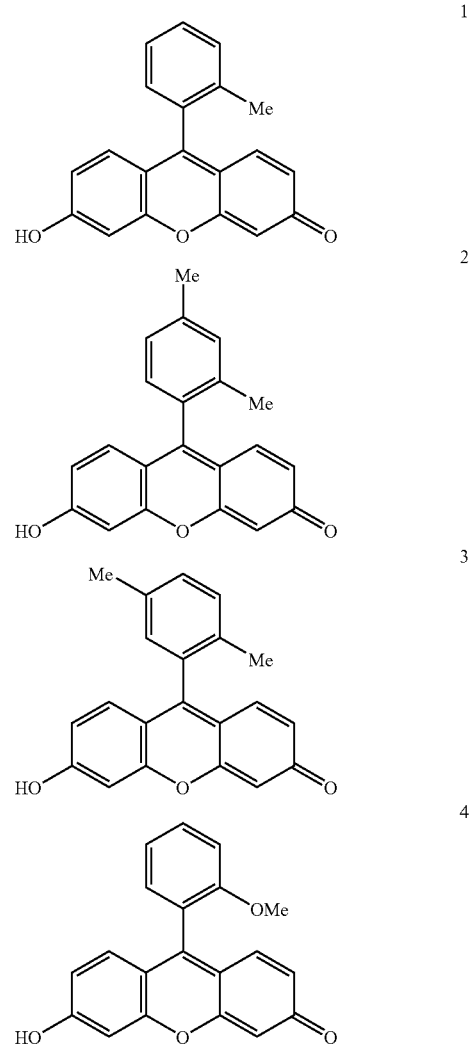

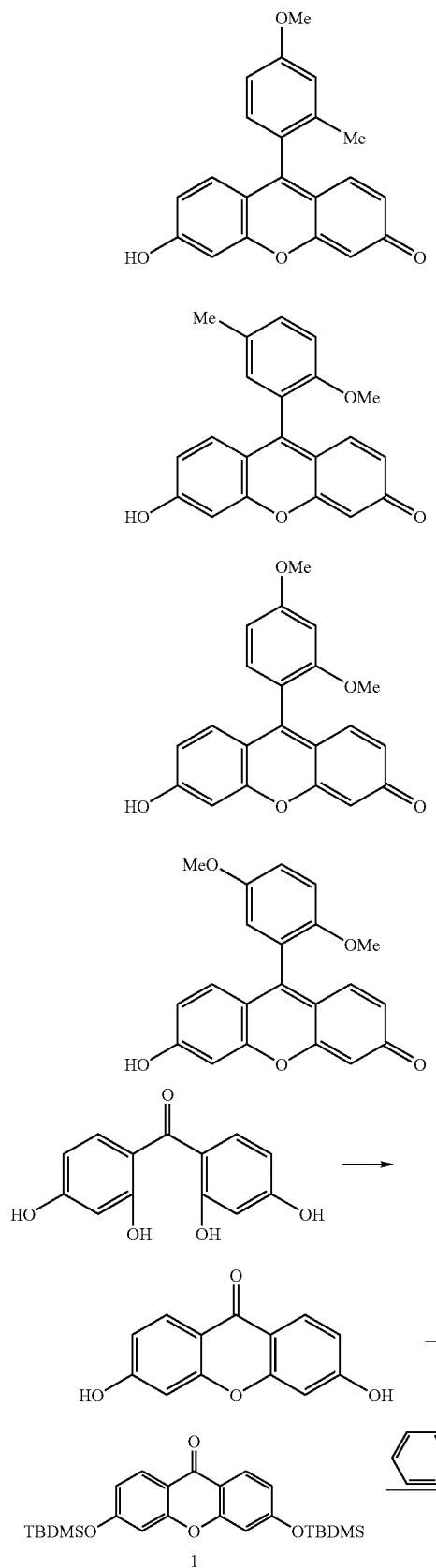

Xanthone was prepared according to the method described in Proc. Indian. Acad. Sci. Sect. A., 57, 280 (1963), and the resulting xanthone was converted to di(tert-butyldimethylsilyl) protected form (xanthone-TBDMS) (J. Biol. Chem., 264, 14, 8171 (1989)). Mg (109 mg, 4.50 mmol) was placed in a well-dried vessel, and stirred for 180 minutes at 250° C. while being kept under reduced pressure with a vacuum pump. After the vessel was cooled, the atmosphere in the vessel was substituted with argon, 2-bromotoluene (77 mg, 0.45 mmol) dissolved in distilled THF (2 ml) was added to the vessel, which was then gradually heated up to 60° C. When the color of the reaction solution was turned dark green, the solution was cooled with ice. Xanthone-TBDMS (137 mg, 0.300 mmol) dissolved in distilled THF (2 ml) was added to the reaction solution, and stirred for 10 minutes. 10 mL of 2N HCl solution was added and stirred to deposit yellow solid. The solid was collected by filtration, washed with a small amount of THF, and dried to obtain yellow solid (87 mg, yield 96%).

$^1$H-NMR (300 MHz, DMSO) δ 2.00 (3H, s), 7.01 (2H, d, J=9.15 Hz), 7.10 (2H, s), 7.21 (2H, d, J=9.15 Hz), 7.31 (1H, d, J=7.14 Hz), 7.52 (3H, m)

MS (EI) 302 (M$^+$)

Compound 2 to Compound 8 were obtained in a similar manner.

Compound 2
$^1$H-NMR (300 MHz, DMSO) δ 1.97 (3H, s), 2.42 (3H, s), 7.01 (2H, d, J=9.15 Hz), 7.10 (2H, s), 7.21 (4H, m), 7.34 (1H, s)
MS (E1) 316 (M$^+$)

Compound 3
$^1$H-NMR (300 MHz, DMSO) δ 1.95 (3H, s), 2.35 (3H, s), 6.99 (2H, d, J=9.15 Hz), 7.05 (2H, s), 7.12 (1H, s), 7.21 (2H, d, J=9.15 Hz), 7.39 (2H, m)
MS (E1) 316 (M$^+$)

Compound 4
$^1$H-NMR (300 MHz, DMSO) δ 3.70 (3H, s), 7.02 (2H, d, J=9.20 Hz), 7.08 (2H, s), 7.23 (2H, t, J=7.50 Hz), 7.34 (4H, m), 7.68 (1H, m)
MS (E1) 318 (M$^+$)

Compound 5
$^1$H-NMR (300 MHz, DMSO) δ 1.98 (3H, s), 3.86 (3H, s), 6.96 (2H, d, J=9.15 Hz), 7.03 (3H, m), 7.10 (1H, s), 7.23 (1H, d, J=8.22 Hz), 7.28 (2H, d, J=9.15 Hz)
MS (E1) 332 (M$^+$)

Compound 6
$^1$H-NMR (300 MHz, DMSO) δ 2.33 (3H, s), 3.66 (3H, s), 7.07 (2H, d, J=9.15 Hz), 7.14 (3H, m), 7.26 (1H, d, J=8.88 Hz), 7.42 (1H, d, J=9.15 Hz), 7.48 (1H, d, J=8.88 Hz)
MS (E1) 332 (M$^+$)

Compound 7
$^1$H-NMR (300 MHz, DMSO) δ 3.70 (3H, s), 3.91 (3H, s), 6.83 (1H, d, J=8.43 Hz), 6.89 (1H, s), 7.06 (2H, d, J=9.36 Hz), 7.12 (2H, s), 7.26 (1H, d, J=8.43 Hz), 7.47 (2H, d, J=9.36 Hz)
MS (E1) 348 (M$^+$)

Compound 8
$^1$H-NMR (300 MHz, DMSO) δ 3.64 (3H, s), 3.76 (3H, s), 6.96 (1H, s), 7.04 (2H, d, J=9.15 Hz), 7.10 (2H, s), 7.23 (1H, d, J=9.15 Hz), 7.30 (1H, d, J=9.15 Hz), 7.23 (2H, d, J=9.15 Hz)
MS (E1) 348 (M$^+$)

Example 2

Correlation between fluorescence quantum yield and the oxidation potential of the benzene ring moiety of each compound prepared above was studied. The results are shown in Table 1 and FIG. 1. As clearly shown by the results in the figure, the fluorescence quantum yield of each compound changed depending on the oxidation potential of the benzene ring moiety. In an alkaline solution at pH 13, the OH group of the xanthene ring dissociates its proton to become an anion, and under this condition, the compound whose oxidation potential is 1.20V or lower became almost non-fluorescent, whereas the compound whose oxidation potential is 1.65V or higher emitted fluorescence with a quantum yield of almost 1. Between the two values, it was observed that the quantum yield decreases according to the decrease in the oxidation potential. An oxidation potential of the benzene ring under the acidic condition at pH 3.4, which has an influence on fluorescence, is different from that under a basic condition, i.e., the compound whose oxidation potential is 1.60V or lower is almost no fluorescent, whereas the compound whose oxidation potential is 1.90V or higher emitted fluorescence with a quantum yield of almost 0.3. It is known that the OH group of the xanthene ring is protonated at pH 3.4, and under this condition, the quantum yield of Fluorescein is about 0.3.

TABLE 1

| R = | Maximum excitation wavelength[a] (nm) | Maximum fluorescence wavelength[a] (nm) | Oxidation potential[b] (V vs SCE) | HOMO energy[c] (hartrees) | $\Phi_{fl}$ (pH 13) | $\Phi_{fl}$ (pH 3.4) |
|---|---|---|---|---|---|---|
| 2-Me (1) | 491 | 510 | 2.19 | −0.2356 | 0.847 | 0.319 |
| 2,4-DiMe (2) | 491 | 510 | 2.08 | −0.2304 | 0.865 | 0.307 |
| 2,5-DiMe (3) | 491 | 510 | 1.98 | −0.2262 | 0.887 | 0.319 |
| 2-OMe (4) | 494 | 515 | 1.75 | −0.2174 | 0.860 | 0.076 |
| 2-Me-4-OMe (5) | 492 | 509 | 1.66 | −0.2141 | 0.840 | 0.010 |
| 2-OMe-5-Me (6) | 494 | 514 | 1.57 | −0.2098 | 0.500 | 0.004 |
| 2,4-DiOMe (7) | 494 | 513 | 1.44 | −0.2063 | 0.200 | 0.001 |
| 2,5-DiOMe (8) | 494 | 512 | 1.26 | −0.1985 | 0.010 | 0.000 |
| Fluorescein | 492 | 511 | n.d.[d] | −0.2646 | 0.850 | n.d.[d] |

[a] Measured in 0.1 N aqueous NaOH
[b] The data were measured in 0.1 M acetonitrile containing tetrabutylammonium perchlorate (TBAP).
[c] The data were obtained with B3LYP/6-31G(d)//B3LYP/6-31G(d) by using Gaussian 98W.
[d] Not measured Example 3

Figure 2:
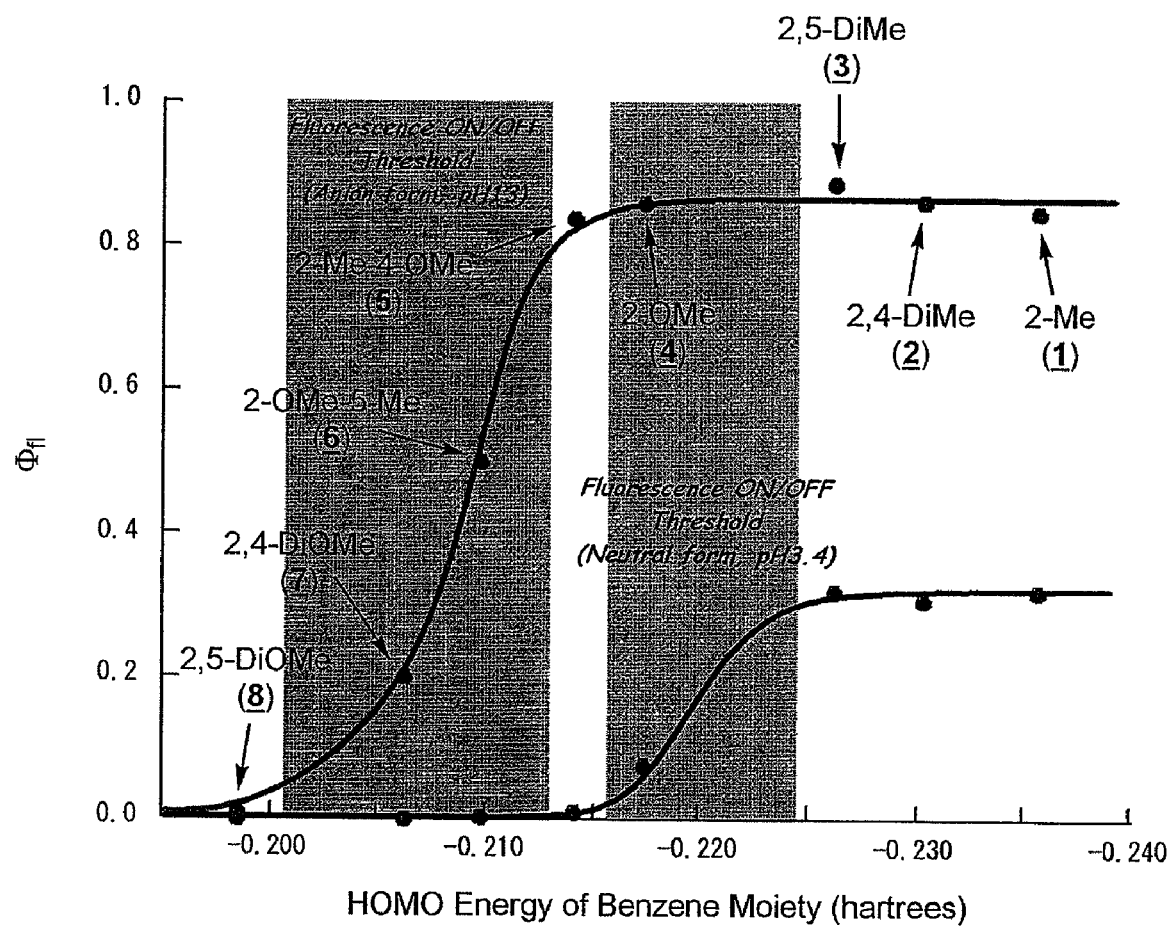
FIG. 2 shows, as for derivatives wherein the carboxy group of fluorescein is converted to an alkyl group or an alkoxy group (Compounds 1 to 8), a correlation between the fluorescence quantum yield of each compound and HOMO energy level of the benzene ring moiety as a PET donor.

Oxidation potential of a compound is generally predictable by quantum chemistry calculation. HOMO energies of the benzene ring moiety of the aforementioned compounds were determined by the density functional method (B3LYP/6-31G (d)), and correlation between the determined values and the fluorescence quantum yield was plotted. As a result, almost the same result was obtained as that of Example 2 wherein oxidation potential was used as a criterion (FIG. 2). From the result, it is proved that the fluorescence property of the compound of the present invention is quantitatively predictable by quantum chemical calculation. On the basis of these findings, a logical designing method of a fluorescent probe of the present invention can be conducted.

Example 4

Figure 3:
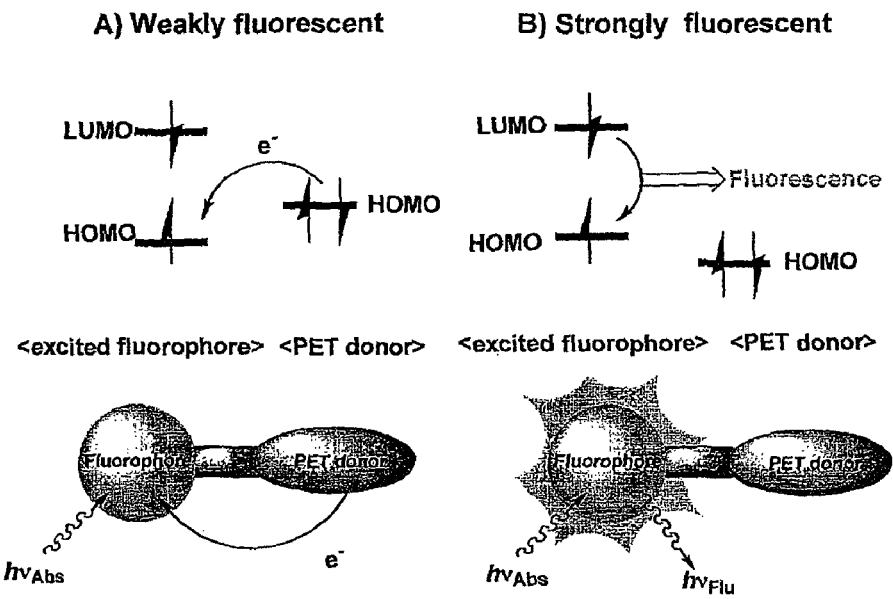
FIG. 3 shows a conceptual diagram of PET and two moieties (i.e, PET donor moiety and a fluorophore) of fluorescein.
Figure 3:
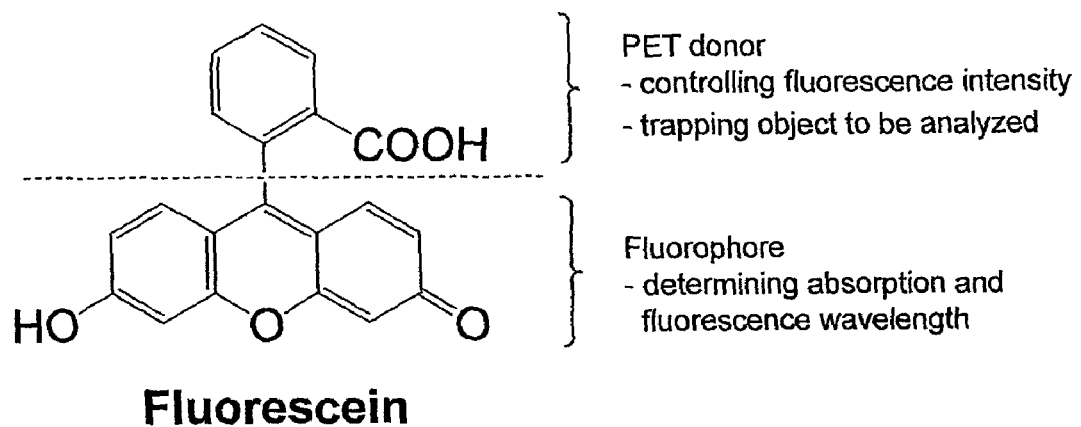

PET (Photoinduced Electron Transfer) is a method for fluorescence quenching, wherein electron transfer from neighboring electron donating moiety (PET donor) occurs to induce fluorescence quenching faster than the rate where the singlet-excited fluorophore generated by irradiation of excitation light returns to the ground state with fluorescence emission. When the compound of the present invention is divided into a xanthene ring moiety which is a fluorophore and a benzene ring moiety which quenches the fluorescence (PET donor) for consideration, if the oxidation potential of the benzene ring is low (i.e., higher electron density, in other words, higher HOMO energy), the fluorescence derived from xanthene is quenched through PET. In fact, the two moieties have revealed to be almost orthogonal to each other from an X-ray crystal structure analysis of fluorescein, and Compounds 1 to 8 have almost the same excitation and fluorescence wavelengths. Accordingly, the hypothesis wherein the compound of the present invention is divided into the two moieties for consideration is believed to be highly appropriate. A conceptual diagram of PET and a conceptual diagram wherein fluorescein was divided into the two moieties are shown in FIG. 3.

The fluorescent probes of the present invention are molecules being no fluorescent when $R^5$ is not cleaved by a measuring object, and have a function to emit fluorescence only when $R^5$ is cleaved by a measuring object. Therefore, an ideal fluorescent probe can be obtained by designing a fluorescent probe whose fluorescence is quenched through PET under the former condition, and causes no PET under the latter condition. For example, it is readily possible to reveal that which level of oxidation potential provides desired properties as a fluorescent probe by the experiment shown in Example 2, and the properties can easily be predicted, even for a new fluorophore, by measuring its reduction potential. In the compounds of the present invention, the oxidation potential of the benzene ring moiety which acts as a PET donor moiety do not change, and the oxidation potential of the xanthene ring moiety changes due to the cleavage of $R^5$ to disturb PET, resulting in emission of fluorescence from the compound of which $R^5$ has been cleaved. Oxidation potentials of the PET donor moiety are predictable by quantum chemistry calculation. According to the steps above, the desired fluorescent probe can be designed without any synthetic process.

Example 5

Preparation of β-Galactosidase Fluorescent Probe

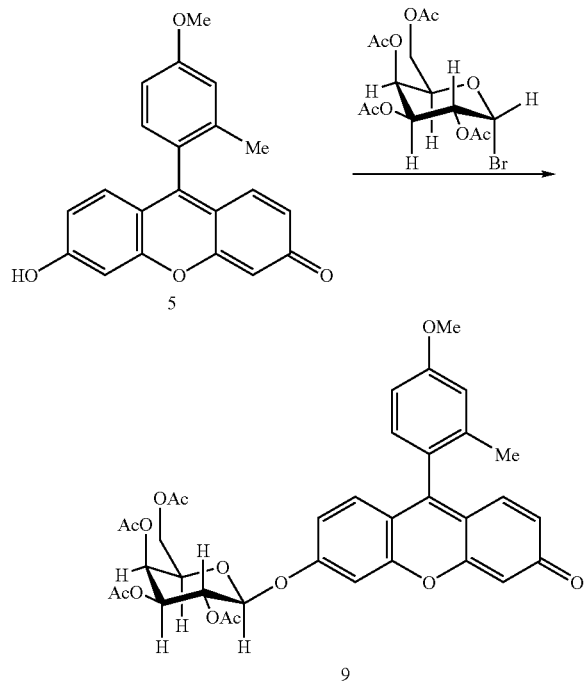

To a well-dried vessel were added anhydrous dimethylformamide (0.5 ml), Compound 5 (10 mg, 30 μmol), $CS_2CO_3$ (100 mg, 300 μmol), and 2,3,4,6-tetra-O-acetyl-α-D-galactopyranosyl bromide (100 mg, 250 μmol). The atmosphere in the vessel was substituted with argon, and the reaction was allowed to continue overnight at room temperature. The precipitates were removed by filtration, and the filtrate was concentrated under reduced pressure. The residue was dissolved in purified water, extracted 3 times with dichloromethane. The organic phase was washed with saturated brine, and dried over anhydrous sodium sulfate. The solvent was evaporated to obtain yellow powder. The powder was purified by silica gel column chromatography using dichloromethane/methanol (100:3) as the eluent to obtain orange powder of Compound 9 (11.3 mg, 57%).

$^1$H NMR (300 MHz/CDCl$_3$) δ 7.15-6.38 (m, 9H), 5.52 (m, 2H), 5.18-5.12 (m, 2H), 4.25-4.12 (m, 3H), 3.92 (s, 3H), 3.70 (s, 3H), 2.19 (s, 3H), 2.13 (s, 3H), 2.07 (s, 3H), 2.03 (s, 3H)

EI-MS: M$^+$=678

Example 6

Measurement of β-Galactosidase Using β-Galactosidase Fluorescent Probe

Compound 9 (tetraacetate compound) obtained in Example 5 was dissolved in anhydrous dimethyl sulfoxide to prepare 100 mM stock solution. This solution was treated with 2 M sodium methoxide at 0° C. for 1 hour to obtain the compound of which four acetyl groups of the saccharide moiety were hydrolyzed (hereafter, this compound is referred to as "fluorescent probe A of the present invention"). Thereafter, the reaction mixture was diluted with a buffer to a desired concentration to terminate the reaction. In the in vitro reaction with β-galactosidase, the final concentration of the fluorescent probe A of the present invention was adjusted to 1 μM, 100 mM sodium phosphate buffer (pH 7.4) was used as a buffer to prepare 3 ml of a solution containing 14.3 mM 2-mercaptoethanol, 1 mM $MgCl_2$, 0.001% dimethyl sulfoxide, 0.01% methanol, and 6 U of β-galactosidase as final concentrations, and the reaction with this solution was allowed in a 1-cm cuvette at 37° C. Change of the fluorescence intensity was observed with a fluorescence spectrometer, Perkin-Elmer LS-50B. The β-galactosidase (molecular weight: 540,000, EC3.2.1.23) was purchased from Sigma-Aldrich. In the assay with live cells, the final concentration of the fluorescent probe A of the present invention was adjusted to 10 μM, and a solution prepared by using physiological saline (pH 7.4, 150 mM NaCl, 4 mM KCl, 2 mM $CaCl_2$, 1 mM $MgCl_2$, 5 mM HEPES, 0.1% glucose, henceforth abbreviated as PSS) as a buffer was used. GP293 cells introduced with LNCX2-lacZ (lacZ-positive cells) were inoculated on a 24-well microplate coated with type 1 collagen, and after the wells were washed twice with PSS, the aforementioned solution of the fluorescent probe A of the present invention was added to the wells, and incubated at room temperature for 30 minutes. GP293 cells not introduced with the vector (lacZ-negative cells) were used as a negative control. Fluorescent images were obtained with an inverted microscope IX70 (Olympus Corporation) provided with DC 300F camera (Leica) as a camera and UPlanFl 10×/0.31 objective lens (Olympus Corporation) as an objective lens under the conditions of excitation wavelength: 488 nm and fluorescence emission wavelength: 510 to 550 nm.

Figure 4:
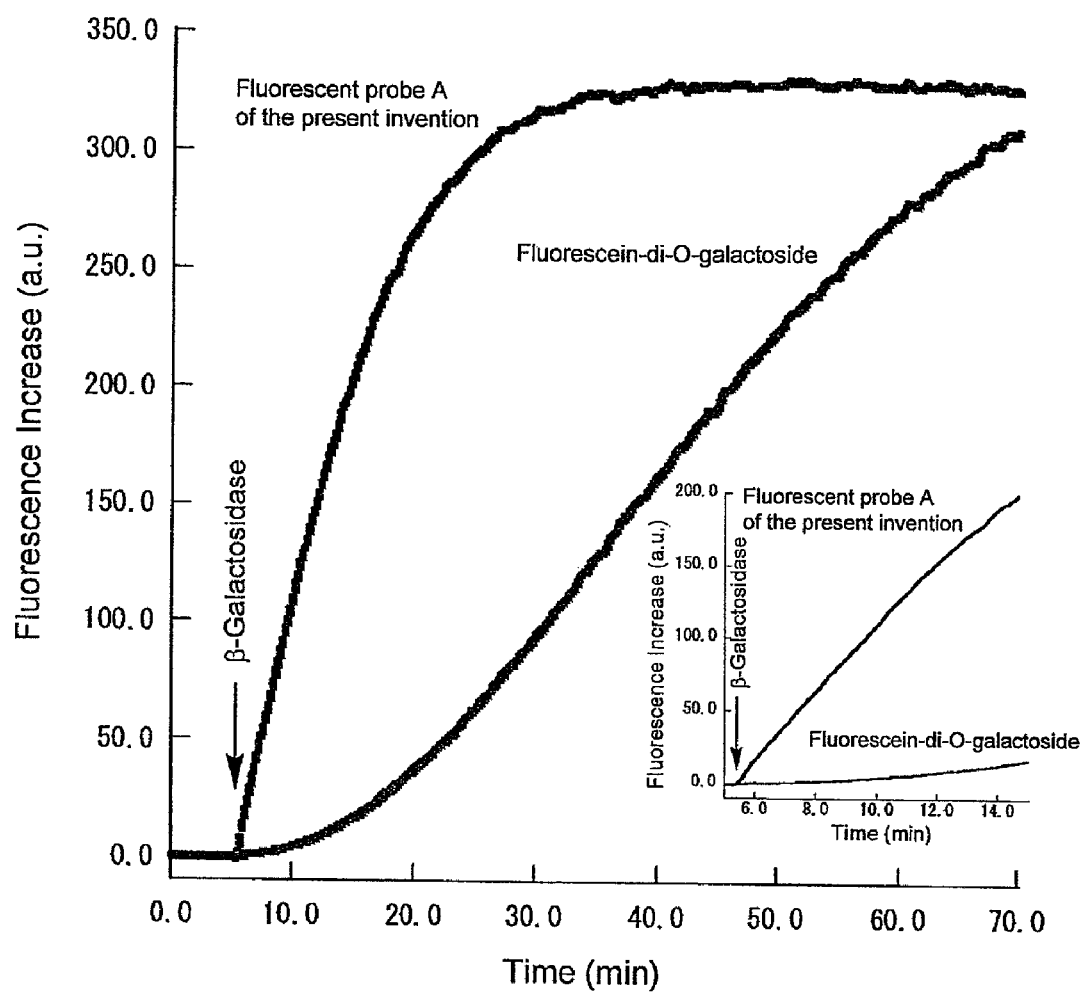
FIG. 4 shows the time course of fluorescence produced by a reaction of the fluorescent probe A of the present invention and β-galactosidase. The graph on the right side of the figure shows change of the fluorescence intensity for the initial 15 minutes of the reaction in an enlarged size.
Figure 5:
FIG. 5 comprises photographs showing the results of the measurement of intracellular β-galactosidase using the fluorescent probe A of the present invention. The photograph on the left side shows the result for lacZ-positive cells, and the photograph on the right side shows the result for LacZ-negative cells.
Figure 5:
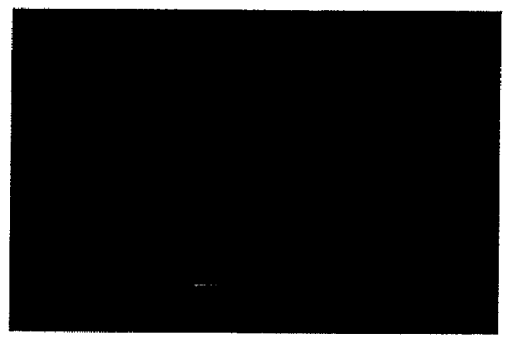

The saccharide moiety of the fluorescent probe A of the present invention was easily cleaved by β-galactosidase, and thus the probe changed from a substantially no fluorescent compound (fluorescence quantum yield=0.009) to a strongly fluorescent compound (fluorescence quantum yield=0.84). The time course of fluorescence changing after the addition of β-galactosidase is shown in FIG. 4. As a comparative compound, known fluorescein-di-O-galactoside (FDG) was used. The fluorescent probe A of the present invention gave a higher reaction rate compared with FDG, and gave a high fluorescence intensity within a short period of time. From the above result, it can be understood that the β-galactosidase activity can be measured with high sensitivity by using the fluorescent probe A of the present invention. The results of the test using live cells are shown in FIG. 5. Fluorescence was observed only in the lacZ-positive cells, and thus it can be understood that the intracellular β-galactosidase can be measured with high sensitivity by using the fluorescent probe A of the present invention. Moreover, it was also demonstrated that the fluorescent probe A of the present invention permiated the cell membranes and easily reached the inside of the cells under physiological conditions.

Example 7

Preparation of Alkaline Phosphatase Fluorescent Probe

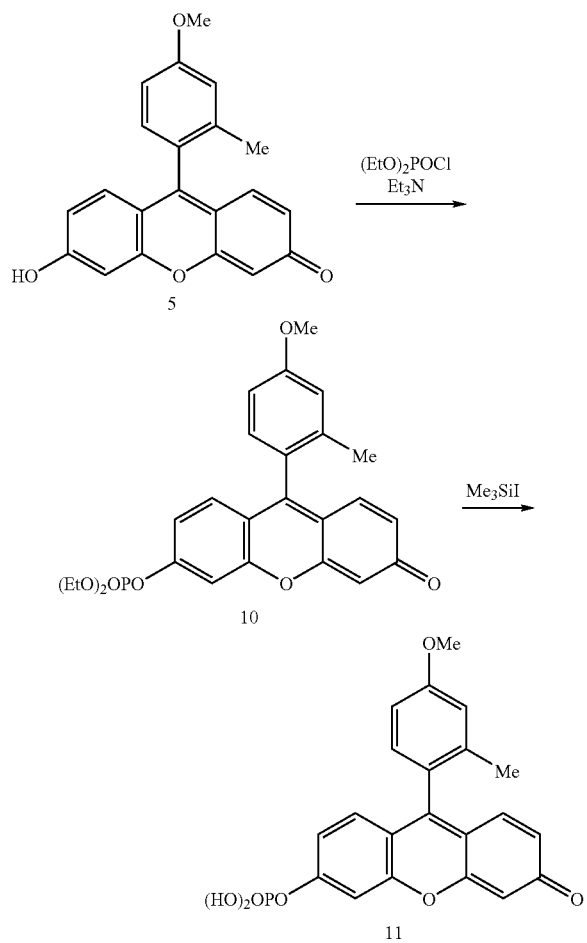

To a well-dried vessel were added anhydrous chloroform (4 ml), Compound 5 (15.7 mg, 47 μmol), triethylamine (16.4 μl, 118 μmol), and diethyl chlorophosphate (6.8 μl, 47 μmol). The atmosphere in the vessel was substituted with argon, and the reaction was allowed to continue overnight at room temperature with stirring. The reaction solvent was evaporated, and the resulting residue was purified with a silica gel column (eluent: dichloromethane/methanol (100:3)) to obtain Compound 10 (26.2 mg, quantitative, orange powder).

$^1$H NMR (300 MHz/CDCl$_3$) δ 1.39 (m, 6H), 2.05 (s, 3H), 3.89 (s, 3H), 4.27 (m, 4H), 6.45 (d, J=2.0 Hz), 6.58 (dd, J=9.7 Hz, 2.0 Hz), 6.86-7.35 (m, 7H)

HR-MS [ESI-MS]: [M+H]$^+$ calcd for 369.14161, found 369.13810

To a well-dried vessel were added anhydrous dichloromethane (1 ml), Compound 10 (26.0 mg, 56 μmol), and iodotrimethylsilane (19.7 μl, 140 μmol). The atmosphere in the vessel was substituted with argon, and the reaction was allowed to continue at room temperature for 1 hour with stirring. The reaction solvent was evaporated, and the resulting residue was purified by using reverse phase preparative TLC RP18W (eluent: acetonitrile/water (1:1)) to obtain Compound 11 (TG-Phos, 1.6 mg, yield: 5.6%, orange powder).

$^1$H NMR (300 MHz/CD$_3$OD) δ 2.02 (s, 3H), 3.90 (s, 3H), 6.48 (d, J=2.0 Hz), 6.60 (dd, J=9.6 Hz, 2.0 Hz), 6.96-7.71 (m, 7H)

HR-MS [ESI-MS]: [M+Na]+ calcd for 411.06336, found 411.05935

$\Phi_{fl}$ (100 mM sodium phosphate buffer, pH 7.4)=0.029

Example 8

In Vitro Alkaline Phosphatase Fluorescence Assay

Figure 6:
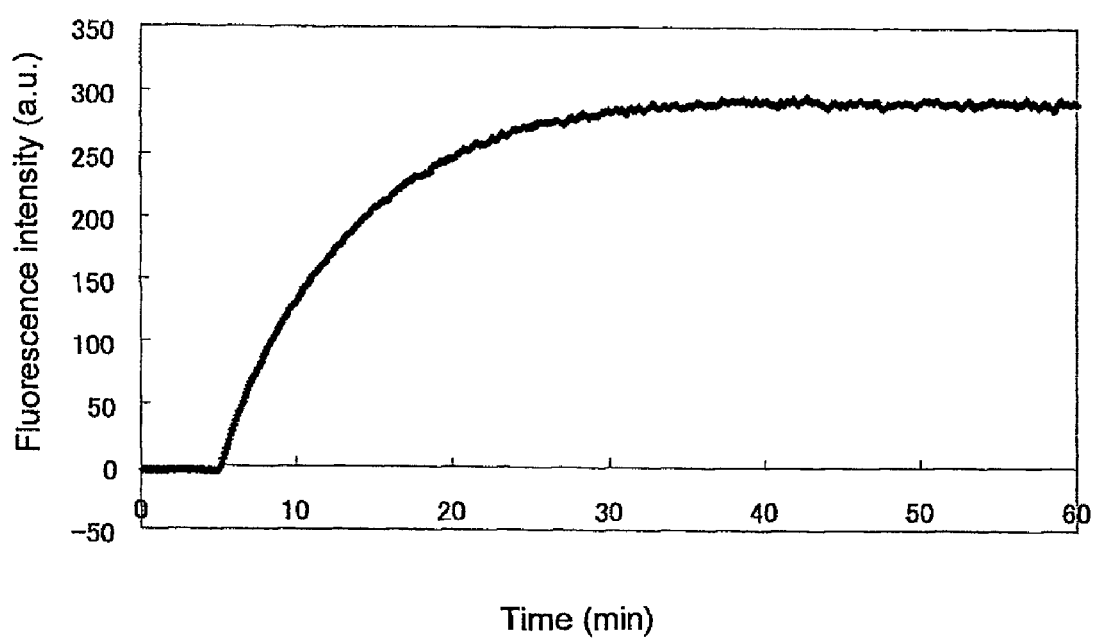
FIG. 6 shows the time course of fluorescence intensity changing of Compound 11 (TG-Phos) when it was brought into contact with an alkaline phosphatase.
Figure 7:
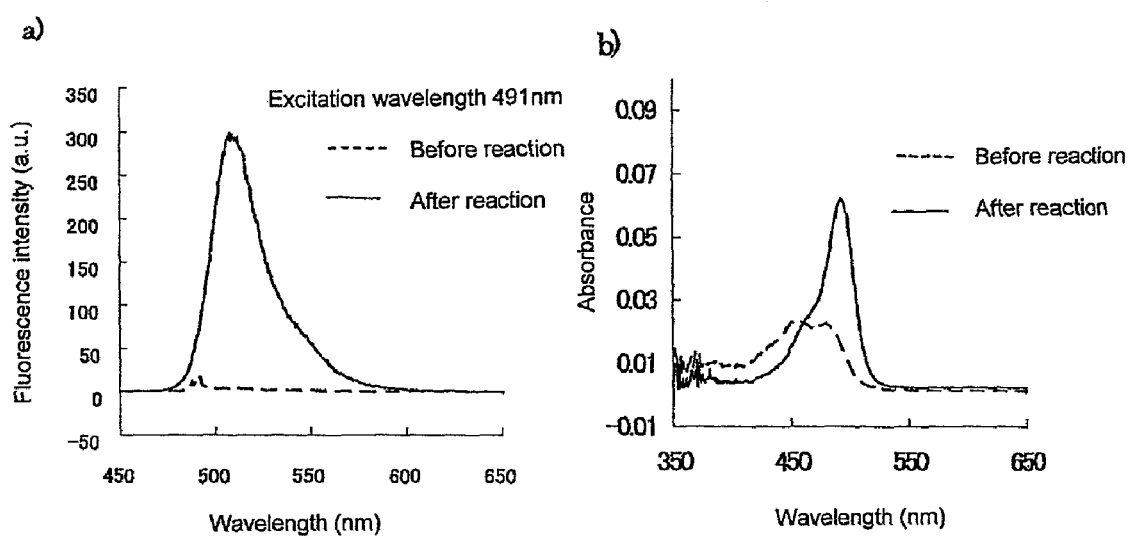
FIG. 7 shows changes of fluorescence spectrum (a) and absorption spectrum (b) of TG-Phos for the periods before and after the reaction with an alkaline phosphatase.

Compound 11 was dissolved in dehydrated methanol to prepare a 1 mM stock solution. Then, the solution was diluted with assay buffer to 1 μM (assay buffer: 0.1 M Tris/hydrochloric acid buffer, pH 7.4, 0.5 mM magnesium chloride, 0.1% methanol). This diluted solution in a volume of 3 ml was transferred to a 1-cm cuvette, and change in fluorescence intensity caused by alkaline phosphatase (0.08 units, added 5 minutes after the start of fluorometry) was measured at 37° C. (FIG. 6). For the measurement, the time course of fluorescence intensity changing at 510 nm was observed with a fluorescence spectrometer, Perkin-Elmer LS-50B, with an excitation wavelength of 491 nm. The alkaline phosphatase (molecular weight: 160 kDa, EC3.1.3.1) was purchased from Sigma-Aldrich. In FIG. 7, changes in the fluorescence spectrum (a) and absorption spectrum (b) before and after the reaction of TG-Phos by alkaline phosphatase are shown.

Example 9

Preparation of Cell-Residing Type β-Galactosidase Fluorescent Probe

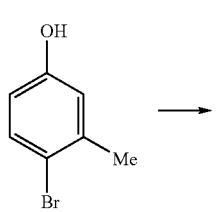

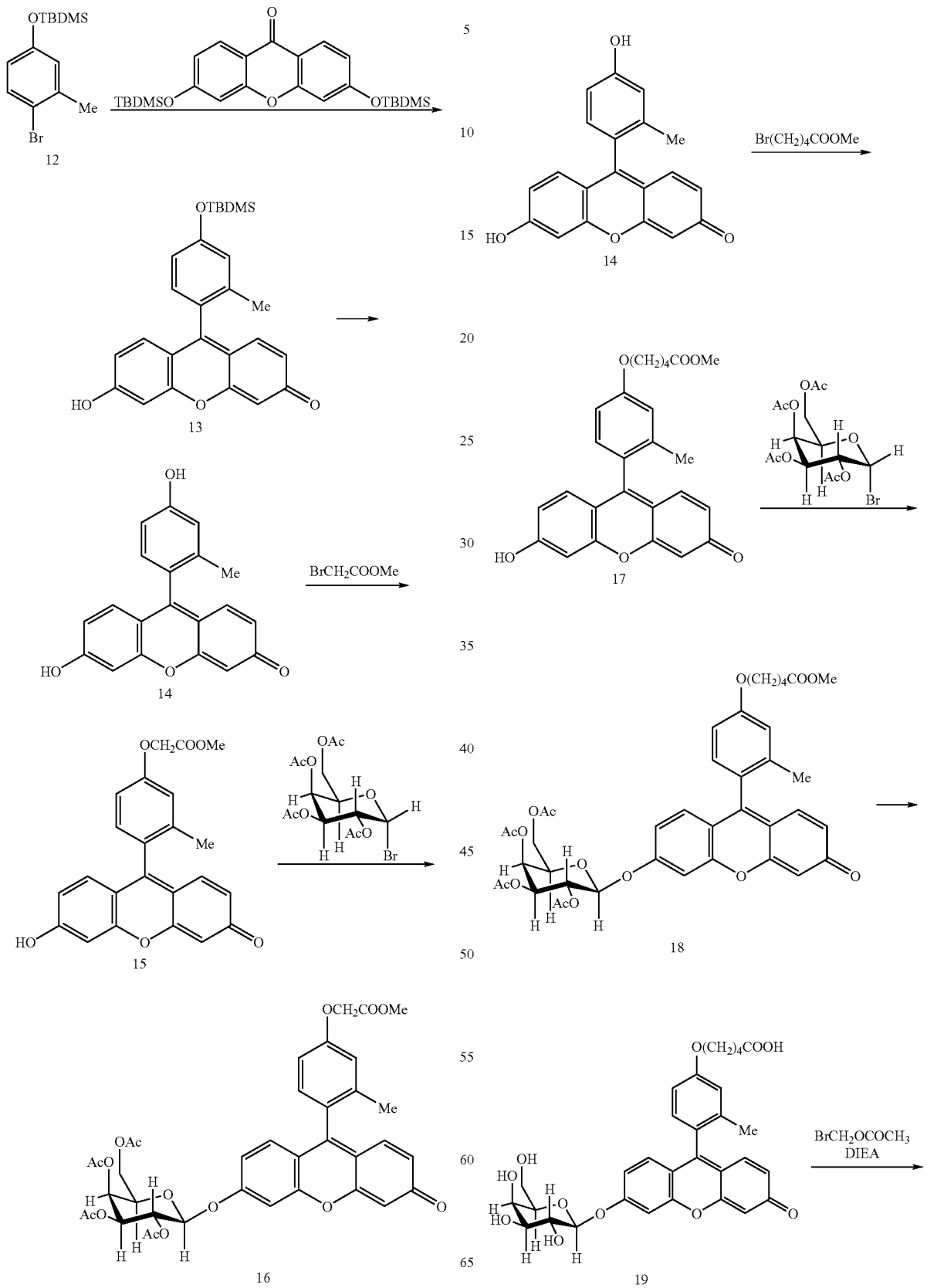

-continued

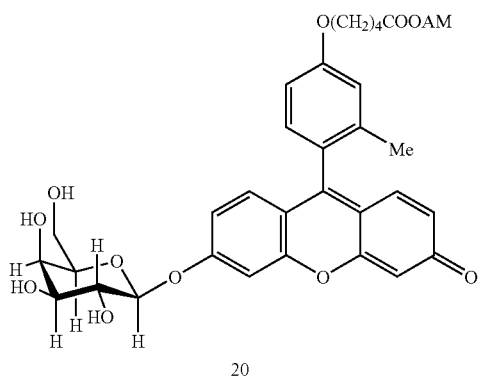

20

AM = —CH₂OCOCH₃

To a well-dried vessel were added anhydrous dimethylformamide (10 ml), 4-bromo-3-methylphenol (2 g, 10.7 mmol), tert-butyldimethylsilyl chloride (TBDMS-Cl) (4.8 g, 30 mmol), and imidazole (3.6 g, 50 mmol). The atmosphere in the vessel was substituted with argon, and the reaction mixture was stirred at room temperature for 3 hours. Then, the solvent was evaporated with a vacuum pump. The resulting residue was dissolved in purified water, and extracted 3 times with dichloromethane. The organic layer was washed with saturated brine, and dried over anhydrous sodium sulfate, and dichloromethane was evaporated to obtain Compound 12 (3.04 g, yield: 94.7%, transparent colorless liquid).

$^1$H NMR ($^{300}$ MHz/CDCl$_3$) δ 7.33 (d, J=8.6 Hz, 1H), 6.72 (d, J=2.9 Hz, 1H), 6.53 (dd, J=8.6 Hz, 2.9 Hz, 1H), 2.32 (s, 3H), 0.97 (s, 9H), 0.18 (s, 6H)

EI-MS: M$^+$=FAB-MS; [M]$^+$=300, 302

Compound 12 (1.28 g, 4.27 mmol) was dissolved in distilled tetrahydrofuran (10 ml) and added by using a syringe to a well-dried 2-neck flask in which atmosphere was substituted with argon. The reaction mixture was maintained at −78° C. on dry ice/acetone, and solution of tert-butyl lithium in n-pentane (4.5 ml, 6.57 mmol) was added portionwise by using a syringe. After stirring for 30 minutes, 3,6-bis-(tert-butyldimethylsilyloxy)xanthone (1.07 g, 2.37 mmol) dissolved in distilled tetrahydrofuran (20 ml) was added portionwise by using a syringe. The reaction mixture was stirred for 30 minutes at −78° C., then neutralized with 2 N hydrochloric acid, and the deposited red substance was collected by filtration. The substance collected by filtration was purified with a silica gel column (eluent: dichloromethane/methanol (100:3 to 100:5)) to obtain Compound 13 (774.6 mg, yield: 82%, orange powder).

$^1$H NMR (300 MHz/CD$_3$OD) δ 7.27 (d, J=9.2 Hz, 2H), 7.15 (d, J=8.3 Hz, 1H), 7.01-6.86 (m, 6H), 2.01 (s, 3H), 1.06 (s, 9H), 0.31 (s, 6H)

FAB-MS; [M+1]$^+$=433

Compound 13 (2.62 g, 6.2 mmol) was dissolved in distilled tetrahydrofuran (200 ml), and 1 M solution of tetrabutylammonium fluoride (TBAF) in tetrahydrofuran (6.2 ml, 6.2 mmol) was added. The atmosphere in the vessel was substituted with argon, and after the reaction mixture was stirred at room temperature for 2 hours, the solvent was evaporated. The resulting residue was purified with a silica gel column (eluent: dichloromethane/methanol (100:5 to 100:7)) to obtain Compound 14 (1.13 g, yield: 57.7%, orange powder).

$^1$H NMR (300 MHz/CD$_3$OD) δ 7.06 (d, J=9.7 Hz, 2H), 6.94 (d, J=8.2 Hz, 1H), 6.78 (d, J=2.4 Hz, 1H), 6.74 (dd, J=8.2 Hz, 2.4 Hz, 1H), 6.63 (dd, J=9.7 Hz, 2.0 Hz, 2H), 6.63 (d, J=2.0 Hz, 2H), 1.88 (s, 3H)

HR-MS (ESI-MS): [M+H]$^+$ calcd for 319.09703, found 319.09652.

To a well-dried vessel were added anhydrous dimethylformamide (1 ml), Compound 14 (60 mg, 0.18 mmol), bromomethyl acetate (17 μl, 0.18 mmol), and cesium carbonate (400 mg, 1.2 mmol). The atmosphere in the vessel was substituted with argon, and the reaction was allowed to continue overnight at room temperature. The precipitates were removed with a Kiriyama funnel, and the solvent was evaporated with a vacuum pump. The resulting residue was dissolved in purified water, and extracted 3 times with dichloromethane. The organic layer was washed with saturated brine, and dried over anhydrous sodium sulfate, and dichloromethane was evaporated. The resulting residue was purified with a silica gel column (eluent: dichloromethane/methanol (100:5)) to obtain Compound 15 (41.7 mg, yield: 56.9%, red powder).

$^1$H NMR (300 MHz/CDCl$_3$) δ 7.10 (d, J=8.4 Hz, 1H), 7.08 (d, J=9.2 Hz, 2H), 6.95 (d, J=2.5 Hz, 1H), 6.89 (dd, J=8.4 Hz, 2.5 Hz, 1H), 6.84 (d, J=2.0 Hz, 2H), 6.80 (dd, J=9.2 Hz, 2.0 Hz, 2H), 4.73 (s, 2H), 3.86 (s, 3H), 2.03 (s, 3H)

FAB-MS: M+1=391

Φ$_{fl}$ (100 mM sodium phosphate buffer, pH 9.0)=0.87

To a well-dried vessel were added anhydrous dimethylformamide (0.5 ml), Compound 15 (39 mg, 0.1 mmol), cesium carbonate (200 mg, 0.6 mmol), and 2,3,4,6-tetra-O-acetyl-α-D-galactopyranosyl bromide (100 mg, 25 mmol). The atmosphere in the vessel was substituted with argon, and the reaction was allowed to continue overnight at room temperature. The precipitates were removed with a Kiriyama funnel, and the solvent was evaporated with a vacuum pump. The resulting residue was dissolved in purified water, and extracted 3 times with dichloromethane. The organic layer was washed with saturated brine, dried over anhydrous sodium sulfate, and dichloromethane was evaporated. The residue was purified with a silica gel column (eluent: dichloromethane/methanol (100:3)) to obtain Compound 16 (2-Me 4-OCH$_2$COOMe TG-β Gal, 41.8 mg, yield: 58.1%, orange powder).

$^1$H NMR (300 MHz/CDCl$_3$) δ 7.10-6.80 (m, 7H), 6.57 (dd, J=9.7 Hz, 1.9Hz, 1H), 6.40 (d, J=1.9Hz, 1H), 5.57-5.48 (m, 2H), 5.18-5.12 (m, 2H), 4.73 (s, 2H), 4.22-4.16 (m, 3H), 3.87 (s, 3H), 2.19, 2.13, 2.07, 2.03 (s, 3H×4), 2.05 (s, 3H)

HR-MS (ESI-MS): [M+Na]$^+$ calcd for 743.19519, found 743.19309.

Φ$_{fl}$ (100 mM sodium-phosphate buffer, pH 7.4)=0.069

To a well-dried vessel were added anhydrous dimethylformamide (1 ml), Compound 14 (63.8 mg, 0.20 mmol), methyl 5-bromovalerate (21 μl, 0.18 mmol), and cesium carbonate (400 mg, 1.2 mmol). The atmosphere in the vessel was substituted with argon, and the reaction was allowed to continue overnight at room temperature. The precipitates were removed with a Kiriyama funnel, and the solvent was evaporated with a vacuum pump. The resulting residue was dissolved in purified water, and extracted 3 times with dichloromethane. The organic layer was washed with saturated brine, dried over anhydrous sodium sulfate, and dichloromethane was evaporated. The residue was purified with a silica gel column (eluent: dichloromethane/methanol (100:5)) to obtain Compound 17 (53.7 mg, yield: 61.9%, red powder).

$^1$H NMR (300 MHz/CDCl$_3$) δ 7.10 (d, J=9.2 Hz, 2H), 7.07 (d, J=8.3 Hz, 1H), 6.91-6.84 (m, 4H), 6.81 (dd, J=9.2 Hz, 2.0 Hz, 2 H), 4.06 (m, 2H), 3.70 (s, 3H), 2.45 (m, 2H), 2.02 (s, 3H), 1.88 (m, 4H)

HR-MS (ESI-MS): [M+Na]$^+$ calcd for 455.14706, found 455.14692.

Φ$_{fl}$ (100 mM sodium phosphate buffer, pH 9.0)=0.82

To a well-dried vessel were added anhydrous dimethylformamide (0.5 ml), Compound 17 (18.2 mg, 42 µmol), cesium carbonate (250 mg, 0.77 mmol), and 2,3,4,6-tetra-O-acetyl-β-D-galactopyranosyl bromide (100 mg, 25 mmol). The atmosphere in the vessel was substituted with argon, and the reaction was allowed to continue overnight at room temperature. The precipitates were removed with a Kiriyama funnel, and the solvent was evaporated with a vacuum pump. The resulting residue was dissolved in purified water, and extracted 3 times with dichloromethane. The organic layer was washed with saturated brine, dried over anhydrous sodium sulfate, and dichloromethane was evaporated. The residue was purified with a silica gel column (eluent: ethyl acetate) to obtain Compound 18 (25 mg, yield: 78%, orange powder).

$^1$H NMR (300 MHz/CDCl$_3$) δ 7.08-6.80 (m, 7H), 6.57 (dd, J=9.7 Hz, 2.0 Hz, 1H), 6.39 (d, J=2.0 Hz, 1H), 5.56-5.48 (m, 2H), 5.18-5.12 (m, 2H), 4.22-4.11 (m, 3H), 4.06 (m, 2H), 3.70 (s, 3H), 2.19, 2.13, 2.07, 2.03 (s, 3H×4), 1.88 (m, 4H)

HR-MS (ESI-MS): [M+Na]$^+$calcd for 785.24214, found 785.23729.

Φ$_{fl}$ (100 mM sodium phosphate buffer, pH 7.4)=0.005

Compound 18 (37.7 mg, 0.049 mmol) was dissolved in 2 ml of a methanol/water (3:1) solution, and 2 M. aqueous sodium hydroxide (1 ml, 2 mmol) was added. The reaction mixture was stirred at 0° C. for 30 minutes, and then neutralized with Amberlite IR-120 (H$^+$), and the solvent was evaporated. The resulting residue was purified by reverse phase preparative TLC (RP18W) using acetonitrile/water (1:1) as the eluent to obtain Compound 19 (2-Me 4-O(CH$_2$)$_4$COOH TG-βGal, 15.1 mg, yield: 53%, orange powder).

$^1$H NMR (300 MHz/CD$_3$OD) δ 7.26 (d, J=2.2 Hz, 1H), 7.11 (d, J=8.5 Hz, 1H), 7.08 (d, J=9.6 Hz, 1H), 7.03 (d, J=8.2 Hz, 1H), 7.02 (dd, J=8.5 Hz, 2.2 Hz, 1H), 6.94 (d, J=2.3 Hz, 1H), 6.89 (dd, J=8.2 Hz, 2.3 Hz, 1H), 6.53 (dd, J=9.6 Hz, 2.0 Hz, 1H), 6.37 (d, J=2.0 Hz, 1H), 4.01 (m, 2H), 5.00 (dd, 7.7 Hz, 2.6 Hz, 1H), 3.83 (d, J=3.3 Hz, 1H), 3.82-3.64 (m, 4H), 3.53 (dd, 9.7 Hz, 3.3 Hz, 1H), 2.17 (m, 2H), 1.93 (s, 3H), 1.74 (m, 4H)

HR-MS (ESI-MS): [M+Na]$^+$ calcd for 603.18423, found 603.18242.

Compound 19 (2-Me 4-O(CH$_2$)$_4$COOH TG-β Gal, 10 mg, 17.2 µmol) was dissolved in methanol/acetonitrile (1 ml/2 ml), bromomethyl acetate (AMBr, 68.5 µl, 690 µmol) dissolved in acetonitrile (2 ml), and diisopropylaminoethane (DIEA, 22.3 µl, 130 µmol) was added. The atmosphere in the vessel was substituted with argon, and after the reaction mixture was stirred at room temperature for 10 hours, the solvent was evaporated. The residue was purified by reverse phase preparative TLC (RP18W) using acetonitrile/water (1:1) as the eluent to obtain Compound 20 (2-Me 4-O(CH$_2$)$_4$COOAM TG-β Gal, 10.9 mg, yield: 97%, orange powder).

$^1$H NMR (300 MHz/CD$_3$OD) δ 7.28 (d, J=2.2 Hz, 1H), 7.13-6.88 (m, 6H), 6.53 (dd, J=9.7 Hz, 2.0 Hz, 1H), 6.38 (dd, J=2.0 Hz, 1H), 5.65 (s, 2H), 4.02 (m, 2H), 5.01 (dd, 8.1 Hz, 2.8 Hz, 1H), 3.83 (d, J=3.1 Hz, 1H), 3.79-3.65 (m, 4H), 3.53 (dd, 9.5 Hz, 3.6 Hz, 1H), 2.42 (m, 2H), 1.99 (s, 3H), 1.94 (s, 3H), 1.78 (m, 4H)

HR-MS (ESI-MS): [M+Na]$^+$ calcd for 675.20536, found 675.20359

Φ$_{fl}$ (100 mM sodium phosphate buffer, pH 9.0)=0.008

Example 10

In Vitro β-Galactosidase Fluorescence Assay

Figure 8:
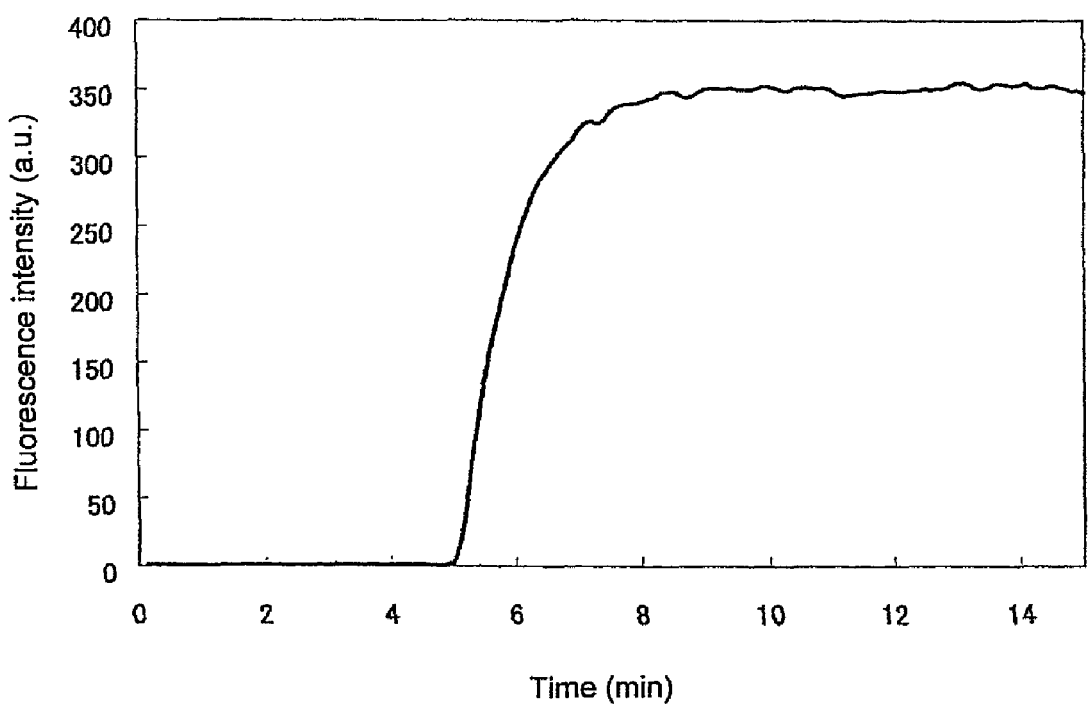
FIG. 8 shows the time course of fluorescence intensity changing of 2-Me 4-O(CH₂)₄COOAM TG β-Gal obtained in Example 9 when it was brought into contact with β-galactosidase.
Figure 9:
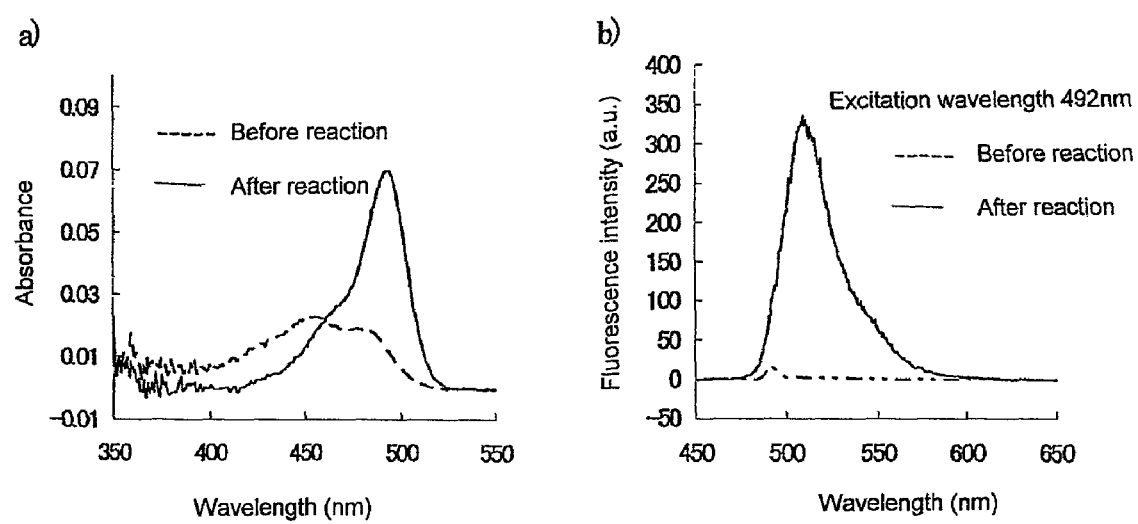
FIG. 9 shows changes of fluorescence spectrum (a) and absorption spectrum (b) of 2-Me 4-O(CH₂)₄COOAM TG β-Gal for the periods before and after the reaction with β-galactosidase.

2-Me 4-O(CH$_2$)$_4$COOAM TG-β Gal was dissolved in anhydrous dimethyl sulfoxide to prepare a 10 mM stock solution. Then, the solution was diluted with assay buffer to 1 µM (assay buffer: 0.1 M sodium phosphate buffer, pH 7.4, 14.3 mM 2-mercaptoethanol, 1 mM magnesium chloride, 0.01% dimethyl sulfoxide). This diluted solution in a volume of 3 ml was transferred to a 1-cm cuvette, and change in fluorescence intensity caused by β-galactosidase (6 units, added 5 minutes after the start of fluorometry) was measured at 37° C. (FIGS. 8 and 9). For the measurement, the time course of fluorescence intensity changing was observed at 509 nm with a fluorescence spectrometer, Perkin-Elmer LS-50B, with excitation wavelength of 492 nm. The β-galactosidase (molecular weight: 540,000, EC3.2.1.23) was purchased from Sigma-Aldrich.

Example 11

β-Galactosidase Fluorescence Assay in Live Cell System

Figure 10:
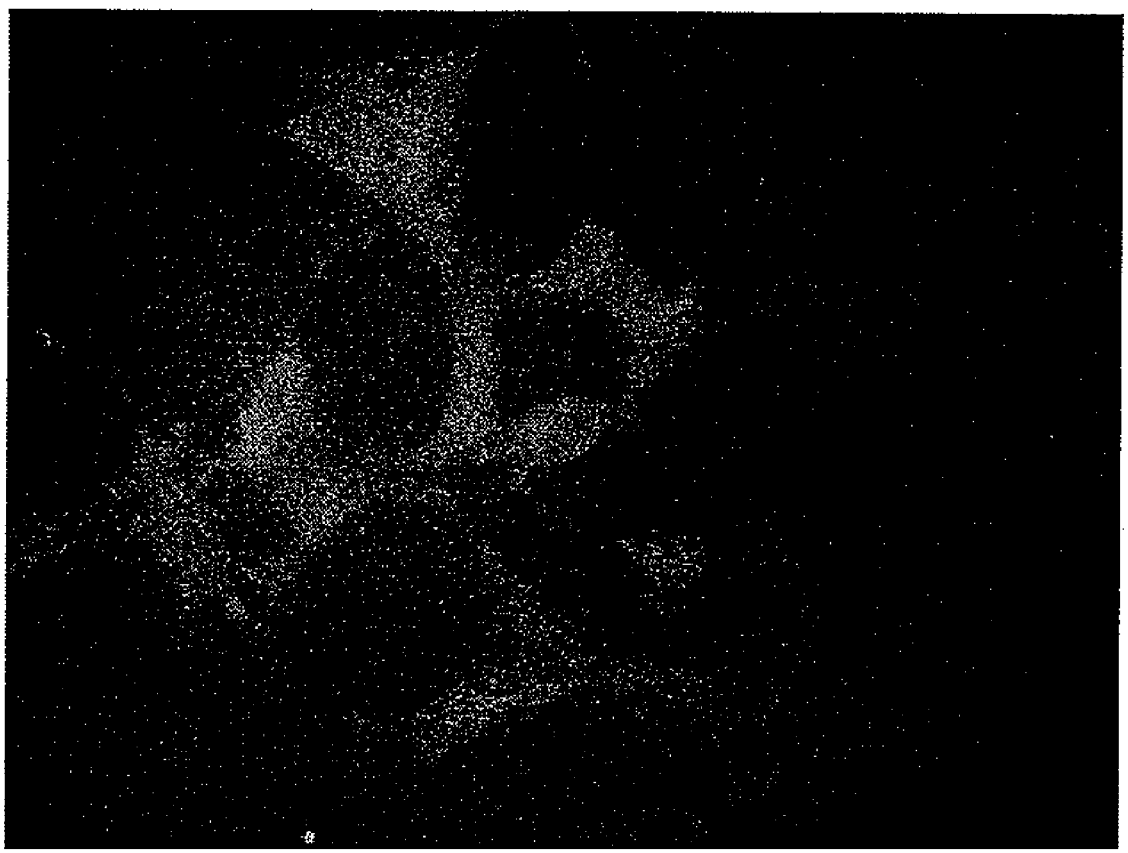
FIG. 10 is a photograph showing the result of β-galactosidase fluorescence assay performed in a live cell system by using 2-Me 4-O(CH₂)₄COOAM TG β-Gal.

In the assay with live cells, the final concentration of 2-Me 4-O(CH$_2$)$_4$COOAM TG-β Gal was adjusted to about 10 µM with physiological saline (pH 7.4, 150 mM NaCl, 4 mM KCl, 2 mM CaCl$_2$, 1 mM MgCl$_2$, 5 mM HEPES, 0.1% glucose, henceforth abbreviated as PSS). GP293 cells introduced with LNCX2-lacZ (lacZ-positive cells) were inoculated on a 24-well microplate coated with type 1 collagen, and after the wells were washed twice with PSS, the aforementioned solution of 2-Me 4-O(CH$_2$)$_4$COOAM TG-β Gal was loaded on the plate, and incubated at room temperature for 30 minutes. GP293 cells not introduced with the vector (lacZ-negative cells) were used as a negative control. Fluorescent images were obtained with an inverted microscope IX70 (Olympus Corporation) provided with UApo/340 40×/1.35 objective lens (Olympus Corporation) as an objective lens under the conditions of excitation wavelength: 488 nm and fluorescence emission wavelength: 510 to 550 nm. The results are shown in FIG. 10. The figure shows the result that fluorescence was observed in the inside of the GP293 cells, indicating expression of β-galactosidase.

Example 12

Preparation of β-Lactamase Fluorescent Probe

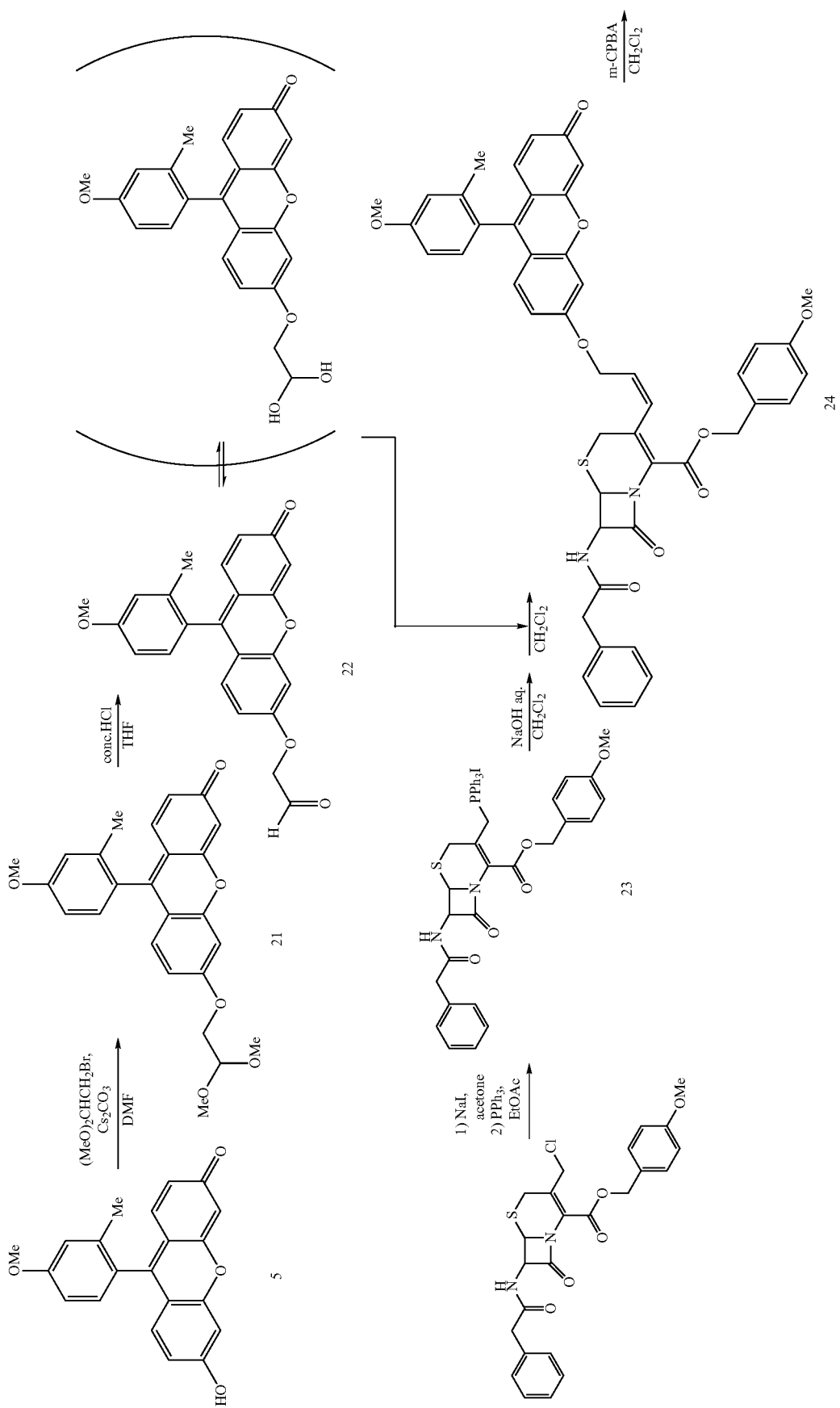

-continued
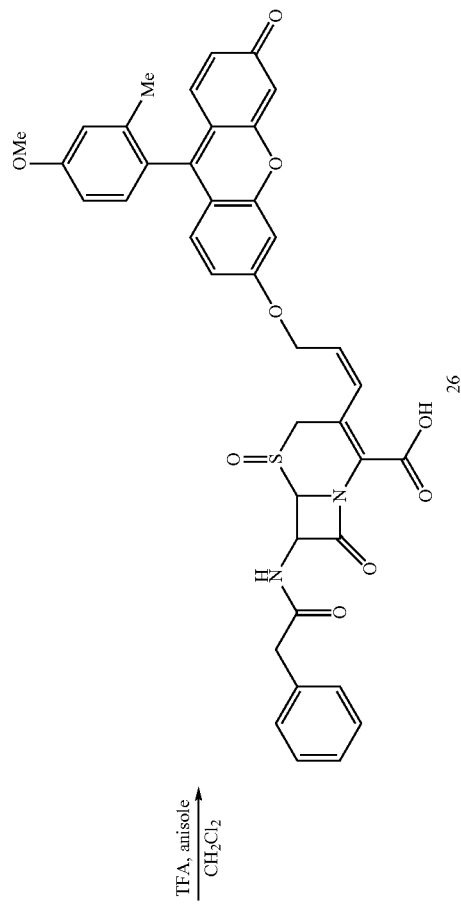
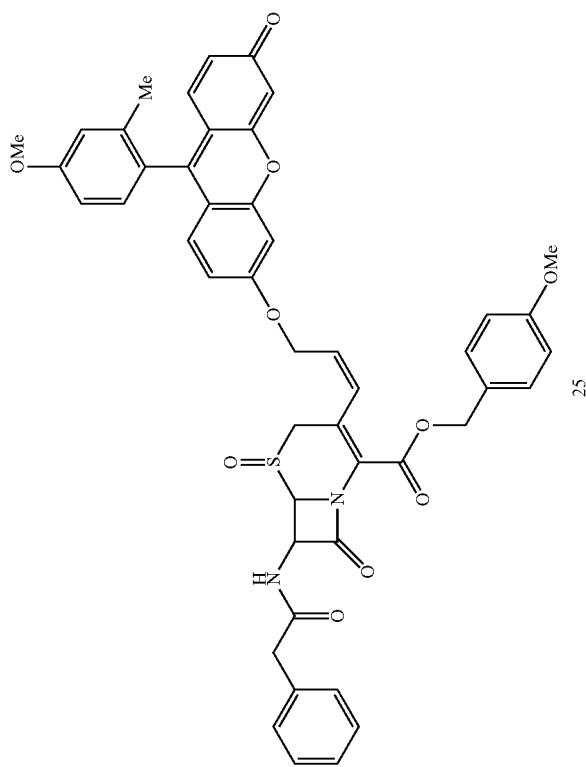

To a well-dried vessel were added anhydrous dimethylformamide (8 ml), Compound 5 (122.4 mg, 0.4 mmol), 2-bromo-1,1-dimethoxyethane (400 μl, 4 mmol), and cesium carbonate (180 mg, 0.6 mmol). The atmosphere in the vessel was substituted with argon, and the reaction was stirred overnight at 115° C. The cesium carbonate was removed with a Kiriyama funnel, and the solvent was evaporated with a vacuum pump. The resulting residue was dissolved in purified water, and extracted 3 times with dichloromethane. The organic layer was washed with saturated brine, and dried over anhydrous sodium sulfate, and dichloromethane was evaporated. The resulting residue was purified with a silica gel column (eluent: dichloromethane/methanol (100:4)) to obtain Compound 21 (78.3 mg, yield: 50.6%, orange powder).

$^1$H NMR (300 MHz/CDCl$_3$) δ 2.04 (s, 3H), 3.48 (s, 6H), 3.89 (s, 3H), 4.11 (d, J=5.1 Hz, 2H), 4.76 (t, J=5.1 Hz, 1H), 6.43 (d, J=2.0 Hz, 1H), 6.57 (dd, J=9.7 Hz, 2.0 Hz, 1H), 6.43-7.14 (m, 7H)

$^{13}$C-NMR (75 MHz/CDCl$_3$) δ 19.91, 54.34, 55.29, 68.13, 101.07, 101.71, 105.66, 111.50, 113.54, 115.02, 115.96, 118.79, 124.48, 129.53, 129.98, 130.31, 130.66, 137.79, 149.44, 154.41, 158.89, 160.32, 162.93, 185.74

HR-MS [ESI-MS]: [M+Na]$^+$ calcd for 443.14706, found 443.14794

To a well-dried vessel were added distilled tetrahydrofuran (8 ml), and Compound 21 (50 mg, 120 μmol). The reaction mixture was maintained at 0° C. on an ice bath, concentrated hydrochloric acid (4 ml) was added slowly, and stirred overnight under argon atmosphere. The solvent was evaporated, and the residue was extracted 3 times with dichloromethane. The organic layer was washed with saturated brine, and dried over anhydrous sodium sulfate, and dichloromethane was evaporated. The resulting residue was purified with a silica gel column (eluent: dichloromethane/methanol (100:4)) to obtain Compound 22 (40.7 mg, yield: 90%, orange liquid).

$^1$H-NMR (300 MHz/CD$_3$OD) δ 2.01 (s, 3H), 3.88 (s, 3H), 4.07 (dd, J=10.3 Hz, 4.95 Hz, 1H), 4.13 (dd, J=10.3 Hz, 4.95 Hz, 1H), 4.90 (t, J=4.95 Hz, 1H), 6.45 (d, J=2.0 Hz)

HR-MS [ESI-MS]:[M+H]$^+$ calcd for 375.12325, found 375.11547

To a well-dried vessel were added distilled acetone (20 ml), 7-phenylacetamido-3-chloromethylcephalosporanic acid p-methoxybenzyl ester (490 mg, 1 mmol), and sodium iodide (750 mg, 5 mmol). The atmosphere in the vessel was substituted with argon, and the reaction mixture was stirred at room temperature for 1.5 hours. The solvent was evaporated, and the residue was extracted with ethyl acetate (25 ml). The organic layer was washed with 10% aqueous sodium thiosulfate, distilled water, and saturated brine, dried over anhydrous sodium sulfate, and triphenylphosphine (320 mg, 1.2 mmol) was added. The atmosphere in the vessel was substituted with argon, and the reaction mixture was stirred overnight at room temperature. The precipitates were collected by filtration using a Kiriyama funnel, and washed with ethyl acetate to obtain Compound 23 (664.3 mg, yield: 78.6%, pale yellow powder).

MR-MS [ESI-MS]: [M−I]$^+$=713

To a well-dried vessel were added distilled dichloromethane (4 ml), Compound 23 (168 mg, 0.2 mmol), and 1 N aqueous sodium hydroxide (2 ml). The reaction mixture was stirred at room temperature for 1 hour, the dichloromethane layer was separated with a separating funnel, and dried over anhydrous sodium sulfate. The organic layer was added to a flask containing Compound 22 (24 mg, 64.2 μmol), and the mixture was stirred overnight at room temperature. The solvent was evaporated, and the resulting residue was purified with a silica gel column (eluent: dichloromethane/methanol (100:4)) to obtain Compound 24 (10.3 mg, yield: 21%, orange powder).

HR-MS (ESI-MS): [M+Na]+ calcd for 831.23522, found 831.23070.

To a well-dried vessel were added distilled dichloromethane (2 ml), Compound 24 (122.6 mg, 0.15 mmol), and m-chloroperbenzoic acid (26 mg, 0.15 mmol). The atmosphere in the vessel was substituted with argon, and the reaction mixture was stirred overnight at 0° C. Dichloromethane was added, washed with 1 N aqueous sodium hydrogencarbonate and saturated brine, dried over anhydrous sodium sulfate, and the solvent was evaporated. The resulting residue was purified with a silica gel column (eluent: dichloromethane/methanol (100:6)) to obtain Compound 25 (105 mg, yield: 84%, orange powder).

HR-MS(ESI-MS): [M+Na]$^+$ calcd for 847.23013, found 847.23210.

To a well-dried vessel were added distilled dichloromethane (3 ml), Compound 25 (40 mg, 0.26 mmol), anisole (150 μl, 1.38 mmol), and trifluoroacetic acid (750 μl, 9.7 mmol). The atmosphere in the vessel was substituted with argon, and the reaction mixture was stirred at 0° C. for 4 hours. The solvent was evaporated, the resulting residue was dissolved in purified water, and extracted 3 times with ethyl acetate. The organic layer was washed with saturated brine, dried over anhydrous sodium sulfate, and ethyl acetate was evaporated. The resulting residue was purified by reverse phase preparative TLC (RP18W, eluent: acetonitrile/water (1:1)) to obtain Compound 26 (TG-β Lac, 9.4 mg, yield: 27.6%, orange powder).

HR-MS (ESI-MS): [M−H]$^-$ calcd for 703.17503, found 703.17719

Example 13

In Vitro β-Lactamase Fluorescence Assay

Figure 11:
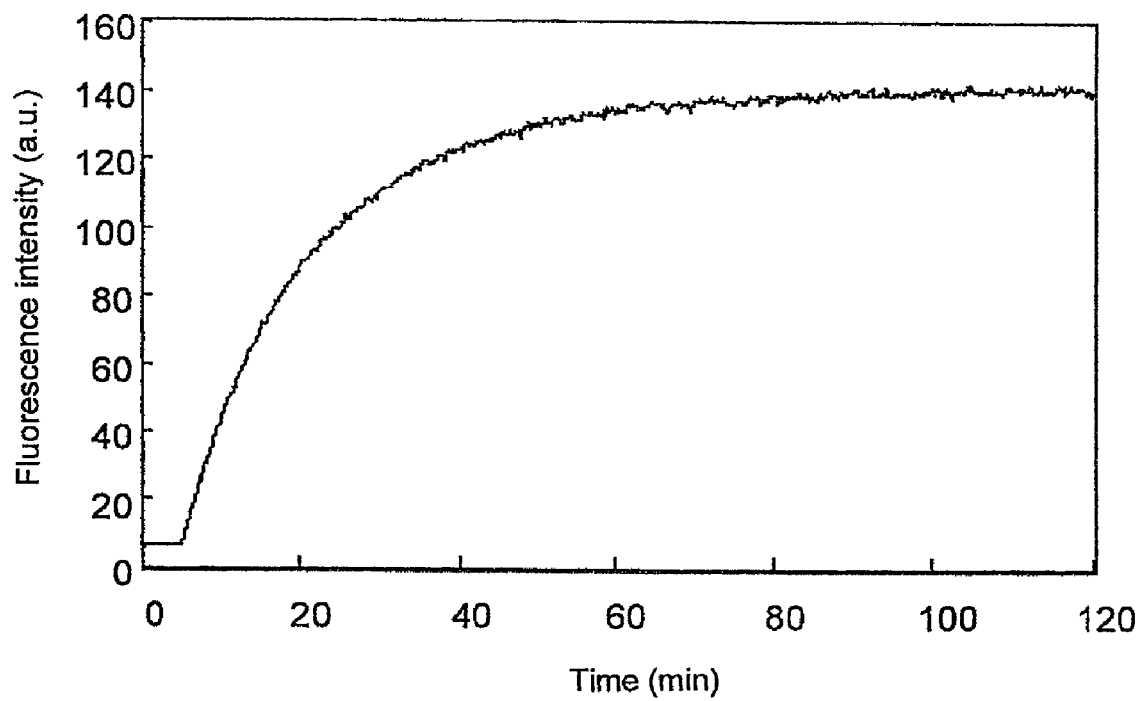
FIG. 11 shows the result of in vitro β-lactamase fluorescence assay using TG-β Lac.

Five minutes after starting measurement, 0.3 unit of β-lactamase was added to an assay buffer (phosphate buffered saline (PBS), Ca$^{2+}$ and Mg$^{2+}$ free, pH 7.4, 0.1% dimethyl sulfoxide) containing TG-β Lac (1 μM), and the time course of fluorescence intensity changing at 510 nm was observed with excitation at 491 nm. The results are shown in FIG. 11.

INDUSTRIAL APPLICABILITY

According to the present invention, a fluorescent probe having an excellent fluorescent property is provided. Further, according to the design method of the present invention, a fluorescent probe having an excellent fluorescent property can be logically designed.

What is claimed is:
1. A fluorescent probe which is represented by the following formula (I):

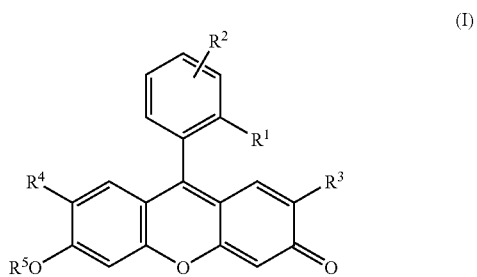

wherein, $R^1$ represents a lower alkyl group or a lower alkoxy group; $R^2$ represents hydrogen atom, a lower alkyl group or a lower alkoxy group; $R^3$ and $R^4$ each independently represents hydrogen atom or a halogen atom; and $R^5$ represents a monovalent group which is cleavable by contact with an enzyme, provided that a combination of $R^1$ and $R^2$ is selected so that the oxidation potential of the benzene ring to which they bind makes:

(1) the compound represented by the formula (I) substantially not fluorescent before the cleavage, and
(2) a compound after the cleavage, which is derived from the compound represented by the formula (I), substantially highly fluorescent after the cleavage.

2. The fluorescent probe according to claim 1, wherein $R^1$ is a lower alkyl group, and $R^2$ is a lower alkoxy group.

3. The fluorescent probe according to claim 1, wherein $R^1$ is a lower alkyl group, and $R^2$ is a lower alkoxy group at the para-position relative to the xanthene ring residue.

4. A fluorescent probe which is represented by the following formula (I):

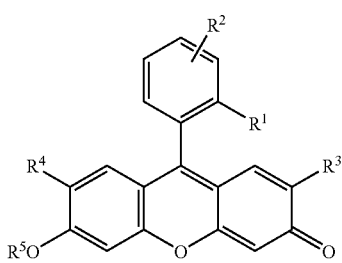

(I)

wherein, $R^1$ represents a monovalent substituent other than hydrogen atom, carboxy group, or sulfo group; $R^2$ represents hydrogen atom, or a monovalent substituent; $R^3$ and $R^4$ each independently represents hydrogen atom or a halogen atom; and $R^5$ is phosphono group cleavable by a phosphatase, provided that a combination of $R^1$ and $R^2$ is selected so that the oxidation potential of the benzene ring to which they bind makes:

(1) the compound represented (I) substantially not fluorescent before the cleavage, and
(2) a compound after the cleavage, which is derived from the compound represented by the formula (I), substantially highly fluorescent after the cleavage.

5. A fluorescent probe which is represented by the following formula (I):

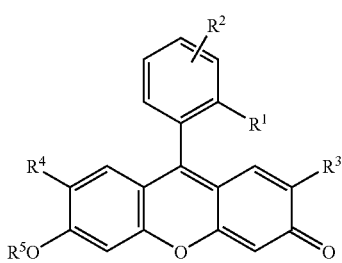

(I)

wherein, $R^1$ represents a monovalent substituent other than hydrogen atom, carboxy group, or sulfo group; $R^2$ represents hydrogen atom, or a monovalent substituent; $R^3$ and $R^4$ each independently represents hydrogen atom or a halogen atom; and $R^5$ is a residue of a saccharide derivative cleavable with a saccharide hydrolase, provided that a combination of $R^1$ and $R^2$ is selected so that the oxidation potential of the benzene ring to which they bind makes:

(1) the compound represented by the formula (I) substantially not fluorescent before the cleavage, and
(2) a compound after the cleavage, which is derived from the compound represented by the formula (I), substantially highly fluorescent after the cleavage.

6. The fluorescent probe according to claim 5, wherein $R^5$ is β-galactopyranosyl group.

7. The fluorescent probe according to claim 5, wherein $R^5$ is β-galactopyranosyl group, and $R^2$ is a carboxy-substituted alkoxy group.

8. A fluorescent probe which is represented by the following formula (I):

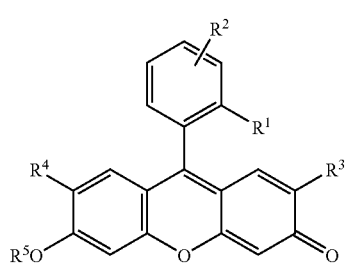

(I)

wherein, $R^1$ represents a monovalent substituent other than hydrogen atom, carboxy group, or sulfo group; $R^2$ represents hydrogen atom, or a monovalent substituent; $R^3$ and $R^4$ each independently represents hydrogen atom or a halogen atom; and $R^5$ is a group containing a cyclic amide cleavable with a β-lactamase, provided that a combination of $R^1$ and $R^2$ is selected so that the oxidation potential of the benzene ring to which they bind makes:

(1) the compound represented by the formula (I) substantially not fluorescent before the cleavage, and
(2) a compound after the cleavage, which is derived from the compound represented by the formula (I), substantially highly fluorescent after the cleavage.

9. The fluorescent probe according to claim 8, wherein the group containing a cyclic amide is a group represented by the following formula;

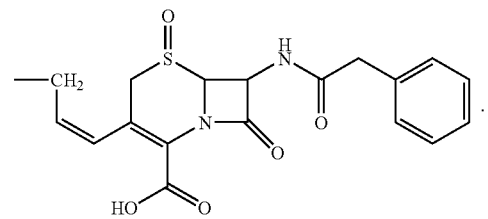

10. The fluorescent probe according to claim 7, wherein $R^2$ is 4-carboxybutoxy group.

* * * * *